United States Patent [19]

Boeck et al.

[11] Patent Number: 5,571,901
[45] Date of Patent: *Nov. 5, 1996

[54] INSECTICIDE AND MITICIDE COMPOSITIONS CONTAINING A83543 COMPOUNDS

[75] Inventors: LaVerne D. Boeck, Indianapolis; Hang Chio, Greenfield; Tom E. Eaton; Otis W. Godfrey, Jr., both of Greenwood; Karl H. Michel; Walter M. Nakatsukasa, both of Indianapolis; Raymond C. Yao, Carmel, all of Ind.

[73] Assignee: DowElanco, Indianapolis, Ind.

[ * ] Notice: The term of this patent shall not extend beyond the expiration date of Pat. No. 5,496,931.

[21] Appl. No.: 479,500

[22] Filed: Jun. 7, 1995

Related U.S. Application Data

[63] Continuation of Ser. No. 406,760, Mar. 17, 1995, Pat. No. 5,496,931, which is a continuation of Ser. No. 141,174, Oct. 22, 1993, abandoned, which is a division of Ser. No. 773,754, Oct. 10, 1991, Pat. No. 5,362,634, which is a continuation of Ser. No. 429,441, Oct. 30, 1989, abandoned, which is a continuation-in-part of Ser. No. 286,591, Dec. 19, 1988, abandoned.

[51] Int. Cl.$^6$ ..................................................... C07H 7/06
[52] U.S. Cl. .......................... 536/7.1; 536/6.5; 424/405; 435/76
[58] Field of Search ........................... 424/405; 435/76; 536/6.5, 7.1

[56] References Cited

U.S. PATENT DOCUMENTS

| | | | |
|---|---|---|---|
| 2,881,162 | 4/1959 | Walasek | 536/7.5 |
| 3,725,385 | 4/1973 | Freiberg | 536/7.1 |
| 4,148,883 | 4/1979 | Celmer et al. | 424/122 |
| 4,206,206 | 6/1980 | Mori et al. | 514/36 |
| 4,213,966 | 7/1980 | Liu et al. | 424/123 |
| 4,224,314 | 9/1980 | Celmer et al. | 424/122 |
| 4,251,506 | 2/1981 | Laby | 424/19 |
| 4,251,511 | 2/1981 | Whaley et al. | 424/122 |
| 4,273,920 | 6/1981 | Nevin | 528/361 |
| 4,293,651 | 10/1981 | Whaley et al. | 435/169 |
| 4,321,329 | 3/1982 | Whaley et al. | 435/252.1 |
| 4,366,308 | 12/1982 | Soma et al. | 536/128 |
| 4,421,760 | 12/1983 | Box | 514/186 |
| 4,448,970 | 5/1984 | Magerlein | 548/311.7 |
| 4,482,707 | 11/1984 | Sakakibara et al. | 536/16.8 |
| 4,501,752 | 2/1985 | Yokoi et al. | 514/414 |
| 4,508,647 | 4/1985 | Hatori et al. | 540/496 |
| 4,514,562 | 4/1985 | Toscano | 536/7.2 |
| 4,515,942 | 5/1985 | Iwasaki et al. | 536/16.8 |
| 4,530,835 | 7/1985 | Bunge et al. | 424/117 |
| 4,560,509 | 12/1985 | Johnson et al. | 540/458 |
| 4,568,740 | 2/1986 | Oppici et al. | 536/7.5 |
| 4,764,602 | 8/1988 | Kumagai et al. | 536/7.1 |
| 4,831,016 | 5/1989 | Mrozik et al. | 514/30 |
| 5,003,056 | 3/1991 | Nishikiori et al. | 536/71 |
| 5,028,536 | 7/1991 | Golik et al. | 435/101 |
| 5,202,242 | 4/1993 | Myndesse et al. | 435/76 |
| 5,227,295 | 7/1993 | Baker et al. | 435/76 |
| 5,362,634 | 11/1994 | Boeck et al. | 435/76 |

FOREIGN PATENT DOCUMENTS

| | | |
|---|---|---|
| 0214731A3 | 3/1987 | European Pat. Off. . |
| 375316A1 | 12/1989 | European Pat. Off. . |
| 2059767 | 9/1979 | United Kingdom . |
| WO9106552 | 5/1991 | WIPO . |
| WO93/09126 | 5/1993 | WIPO . |

OTHER PUBLICATIONS

Sakano et al. (1980), J. Antibiot. (Tokyo), 33(7):683–689.
Brown et al. (1986), J. Liq. Chromatography, 9(4):831–844.
Chen et al. (1981), ACTA Microbiol. Sin., 21(2):192–196 (Biosis abstract).
Drioli (1986), Separation, Recovery and Purification in Biotechnology, 52–66.
Kubo et al. (1985), Analytical Letters, 18(B3):245–260.
Brode et al. (1986), Arzneim–Forsch, 36(3):437–442.
Julien et al. (1988), Clin. Chem., 34(5):966–969.
Chemical Abstracts, vol. 87, No. 24, Dec. 1977, R. Datta et al., "Concentration of Antibiotics by Reverse Osmosis." See p. 310, see the Abstract No. 189423a, Biotechnol. Bioeng. 1977, vol. 19, No. 10, 1419–1429.
Cram et al. (1964), Organic Chemistry, 2nd ed., p. 204.
Journal of American Chemical Society (1992), vol. 114, No. 6, pp. 2260–2262, Evans et al., "Asymmetric Synthesis of the Macrolide (+)–A83543A (Lepicidin) Aglycone." See the whole document.
Chemical Abstracts (1991), vol. 114, No. 80066m, Boeck et al.
ACS Symposium Series, Synthesis and Chemistry of Agrochemicals III, vol. 504, 1992, pp. 214–225, Kirst et al., "Discovery, Isolation, and Structure Elucidation of a Family of Structurally Unique, Fermentation–Derived Tetracyclic Macrolides." See abstract. See p. 216, paragraph 2; p. 217, paragraph 1.
Jacobson, G. K., "Mutations," Chapter 5b of *Biotechnology*, vol. 1, H.–J. Rehm and G. Reeds, eds. (1981).
Journal of the Chemical Society (1964), London, GB, Birch et al., "Studies in Relation to Biosynthesis." Part XXXV. Macrolide Antibiotics to Biosynthesis. Part XII. Methymycin, pp. 5274–5278.
Chemical Abstracts (1979), vol. 90, No. 19, pp. 591, Column 2—p. 592, Column 1, Abstract No. 151957b, Columbus, OH; Inanaga et al., "Synthesis of Methynolide,"& Tennen Yuki Kagobutsu Toronkai Koen Yoshishu, 21st 1978, 324–30 (abstract).
Pickett, J. A. (1988), Chemistry in Britain, 137–142.

(List continued on next page.)

*Primary Examiner*—Gary L. Kunz
*Assistant Examiner*—Kathleen Kahler Fonda
*Attorney, Agent, or Firm*—Andrea T. Borucki

[57] ABSTRACT

Fermentation product A83543, comprising major components A83543A and A83543D and minor components A83543B, A83543C, A83543E, A83543F, A83543G, A83543H and A83543J, is produced by a newly described species, *Saccharopolyspora spinosa*. The A83543 components and their acid-addition salts (A83543 compounds) are useful as insecticides, particularly against Lepidoptera and Diptera species. Insecticidal, miticidal or ectoparasiticidal combinations, compositions and methods are provided.

3 Claims, 17 Drawing Sheets

OTHER PUBLICATIONS

Kirst et al., Tetrahedon Letters (1991), 32(37):4839–4842.
Whaley et al., Tetrahedron Letters (1980), 21:3659–3662.
Kreuzman et al., J. Biological Chemistry (1988), 263(30):15626–15633.
Snyder et al., J. Am. Chem. Soc. (1984), 106:787–789.
Mertz and Yao, Int'l. J. of Systematic Bacteriology (1990), 40(1):34–39.
Celmer et al., J. Am. Chem. Soc. (1980), 102(12):4203–4209.
Aizawa et al. (1979), The Journal of Antibiotics, 32(3):193–196.
Ikeda et al. (1985), The Journal of Antibiotics, 38(3):436–438.
Jomon et al. (1972), The Journal of Antibiotics, 25(5):271–280.
Dybas and Babu (1988), Brighton Crop Protection Conferences, 57–64.
Borchardt et al. (1979), Biochemical and Biophysical Research Communications, 89(3):919–924.
Vedel et al. (1978), Biochemical and Biophysical Research Communications, 85(1):371–376.
Omura (1984), Macrolide Antibiotics, Chapter 13.
Fuller (1978), Biochemical Pharmacology, 27:1981–1983.
Jackson et al. (1988), Abstracts of the 1988 ICAAC.
Umezawa (1980), The Journal of Antibiotics, 33(3):15–26.
Umezawa, Index of Antibiotics from Actinomycetes, vol. 2.
Omura and Tannaka (1984), Macrolide Antibiotics, Chapter 1.
Shulman and Ruby (1987), Antimicrobial Agents and Chemotherapy, 31(6):964–965.
Shulman et al. (1985), The Journal of Antibiotics, 38(11):1494–1498.
Ito and Hirata (1972), Tetrahedron Letters, 12:1185–1188.
Catalogue of Bacteria and Phages, ATCC, 17th ed., 1989.
Derwent Abstract 84–278337/45, SSSE Mar. 16, 1983.
Derwent Abstract 84–252941/41, SSSE Feb. 16, 1983.
Derwent Abstract 92:144960k, Antibiotic N–461.
Derwent Abstract 11667C/07, KAKE May 31, 1978.
Derwent Abstract 92:211459u.
Derwent Abstract 88–095030/14, SSSE 1986.
Derwent Abstract 85–245719/40, SSSE Feb. 1, 1984.
Derwent Abstract 54333S–BCD, Fuji Jan. 17, 1969.
Derwent Abstract JP55000310, Jan. 1980.
Derwent Abstract JP59151896, Aug. 1984.
Derwent Abstract JP62226925, Oct. 1987.
Derwent Abstract JP63045280, Feb. 1988.
Derwent Abstract JP71028833, Aug. 1971.
Derwent Abstract JP59170092, Sep. 1984.
Derwent Abstract JP85053597, Nov. 1985.
Derwent Abstract JP60160888, Aug. 1985.
Derwent Abstract JP73039922.
Biosis Abstract 90:127301 Mertz et al., "Int. J. Syst. Bact." 40(1) 1990 34–39.

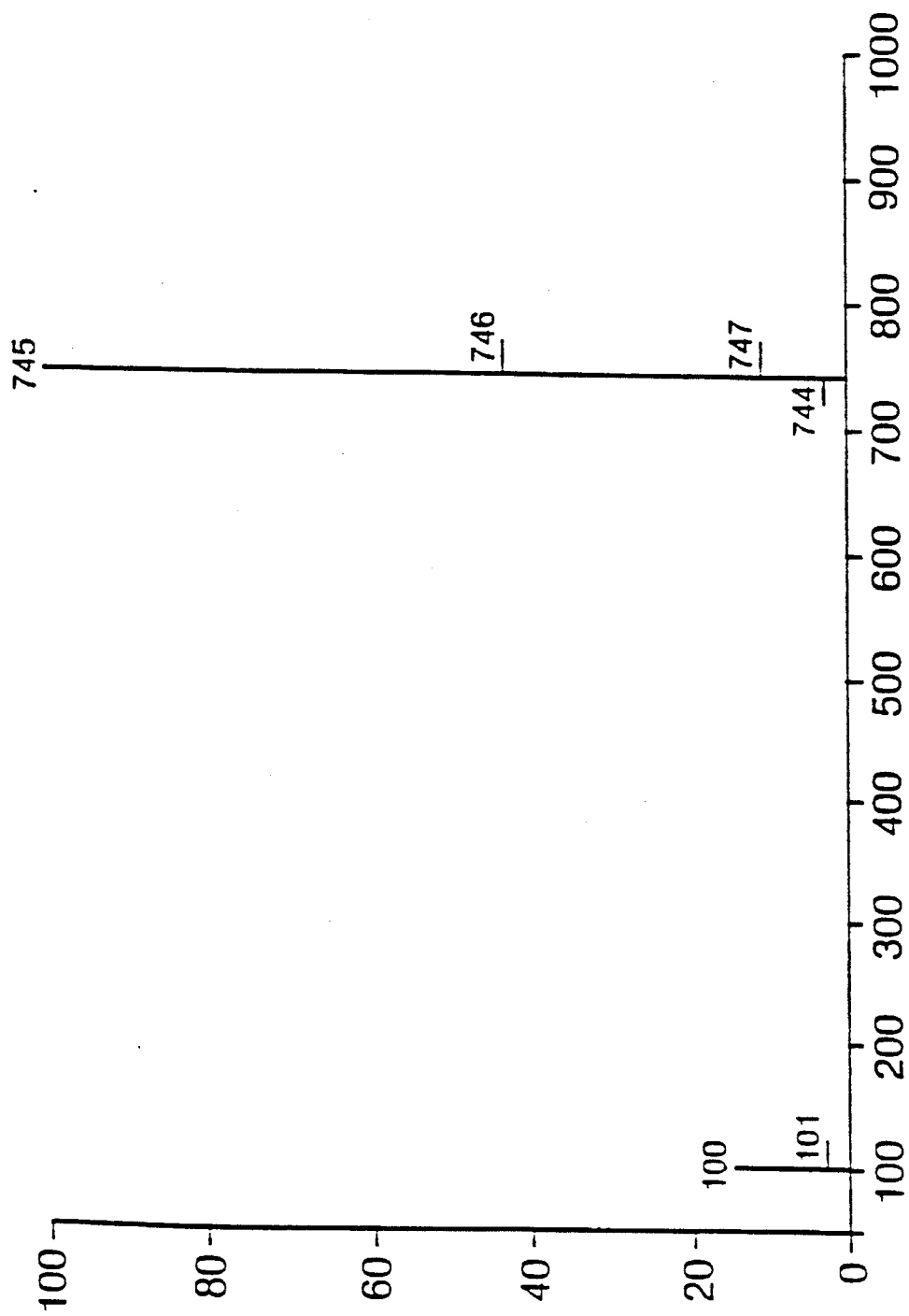

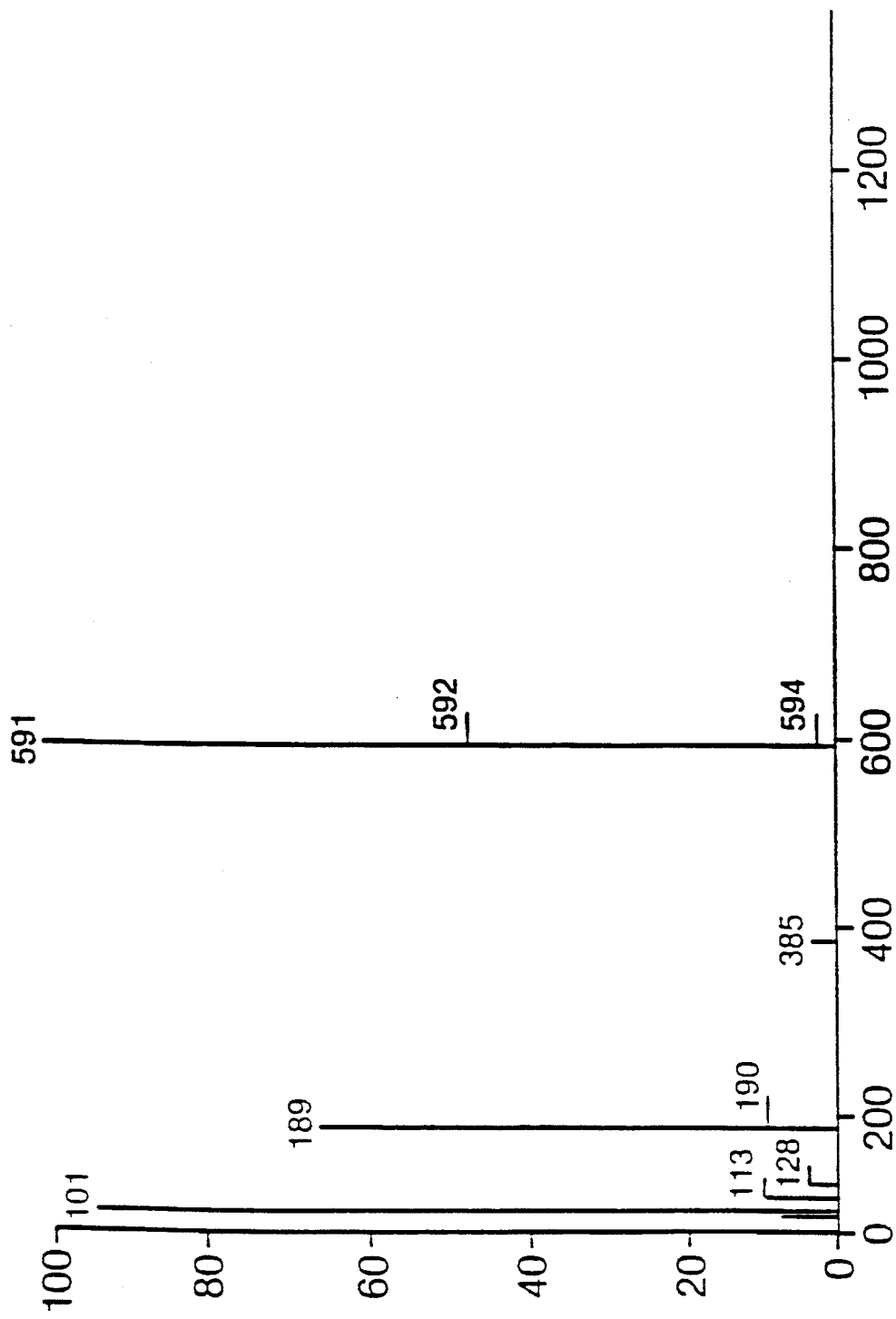

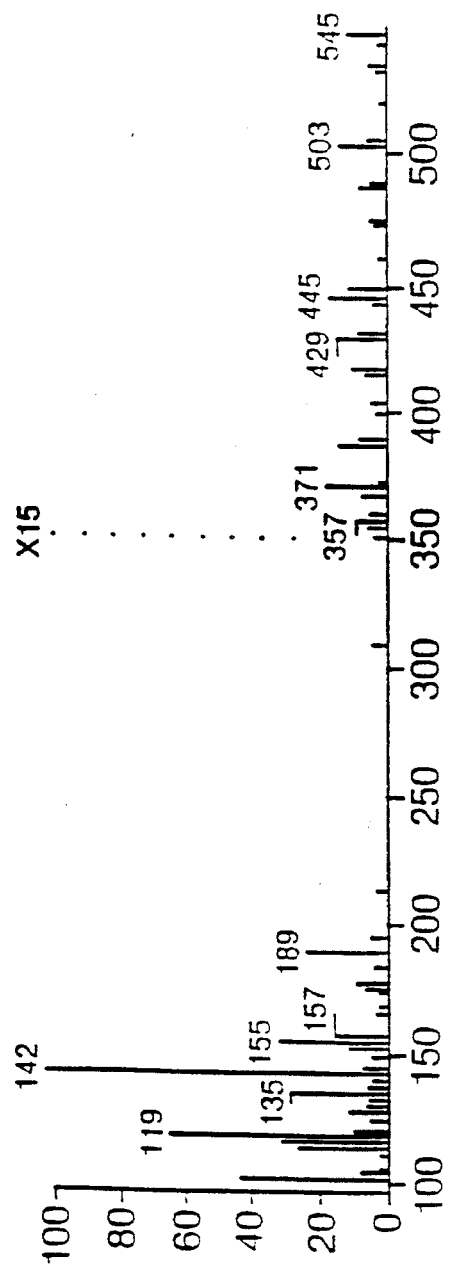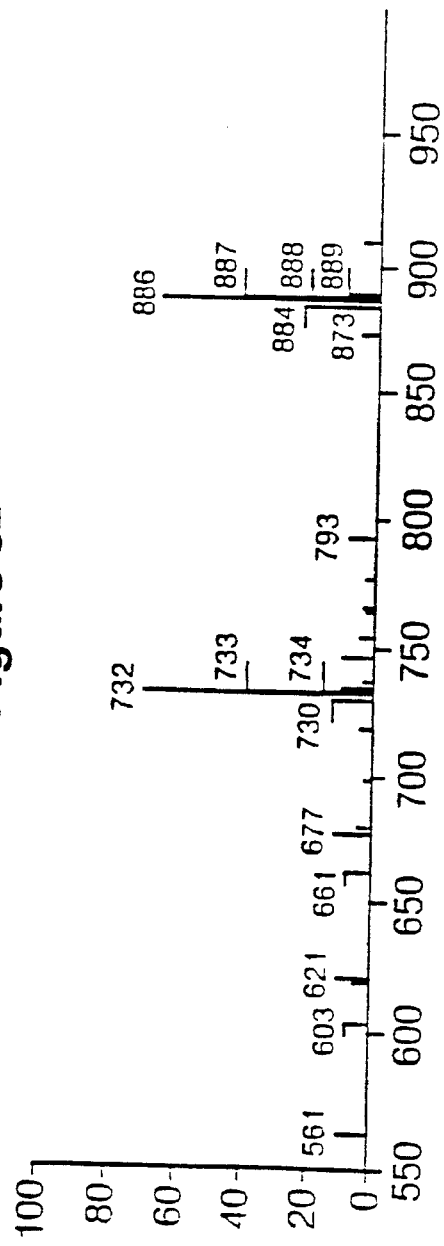

A = $C_8H_{16}NO$, m/z 142
B = $C_8H_{16}NO_2$, m/z 158
C = $C_{33}H_{49}O_8$, m/z 573
D = $C_{24}H_{33}O_8$, m/z 449
E = $C_4H_8O_2$, m/z 88
F = $C_4H_8O_2$, m/z 88
G = $C_9H_{17}O_4$, m/z 189
H − $C_8H_{17}NO_2$ = $C_{24}H_{31}O_4$, m/z 383
I − $C_8H_{17}NO_2$ = $C_{24}H_{31}O_3$, m/z 367

INSECTICIDE AND MITICIDE COMPOSITIONS CONTAINING A83543 COMPOUNDS

CROSS-REFERENCE TO RELATED APPLICATIONS

This is a continuation of application Ser. No. 08/406,760, filed Mar. 17, 1995, which is now U.S. Pat. No. 5,496,931, which is a continuation of No. 08/141,174, filed Oct. 22, 1993, which is abandoned, which was a divisional of U.S. Ser. No. 07/773,754, filed Oct. 10, 1991, which is now U.S. Pat. No. 5,362,634, which is a continuation of U.S. Ser. No. 07/429,441, filed Oct. 30, 1989, which is now abandoned, which is a continuation-in-part of U.S. Ser. No. 07/286,591, filed Dec. 19, 1988, which is now abandoned.

BACKGROUND OF THE INVENTION

1. Field of the Invention

This invention provides a new group of compounds that have excellent insecticidal activity. The invention further provides compositions and combination products that contain a compound of the invention as an active ingredient, insecticidal methods and methods of controlling ectoparasites of domestic animals.

There is a serious need for new insecticides and miticides because target organisms are rapidly developing resistance to insecticides and miticides in current use. Resistance to insecticides in arthropods is widespread, with at least 400 species being resistant to one or more insecticides. Development of resistance to older insecticides, such as DDT, the carbamates, and the organophosphates, is well known. Resistance has even developed, however, to some of the newer pyrethroid insecticides and miticides. A need exists, therefore, for new insecticides and miticides.

The control of ectoparasites, such as fleas, ticks, biting flies and the like, has long been recognized as an important problem in animal husbandry. The traditional treatments for domestic animals were topically applied insecticides, such as the famous dips for sheep. Indeed, such treatments are still in wide use. Currently, however, the thrust of research has been towards compounds which can be administered to the animals, especially orally, and which will control ectoparasites by poisoning the parasite when it ingests the blood of the treated animal.

SUMMARY OF THE INVENTION

This invention relates to fermentation product A83543 comprising individual components A83543A, A83543B, A83543C, A83543D, A83543E, A83543F, A83543G, A83543H, and A83543J and to their salts. A83543 is produced by culturing a member of a newly described species of the genus *Saccharopolyspora*, *Saccharopolyspora spinosa* sp. *nov.*, selected from *S. spinosa* strain NRRL 18395, NRRL 18537, NRRL 18538, or NRRL 18539, or an A83543-producing mutant thereof, under submerged aerobic fermentation conditions.

A83543 and the individual A83543 components are useful for the control of insects, particularly Lepidoptera, such as Southern armyworm, Diptera species, such as blow fly, stable fly and mosquito. Thus, insecticidal compositions and methods for reducing population of insects or mites using A83543 compounds are also part of this invention.

In addition, the amino-sugar can be removed from the A83543 components to give six unique pseudoaglycones, the A83543A, A83543D, A83543E, A83543F, A83543H and A83543J pseudoaglycones. These compounds are useful as intermediates.

This invention also relates to biologically-purified cultures selected from the *Saccharopolyspora spinosa* sp. *nov.* strains NRRL 18395, NRRL 18537, NRRL 18538 or NRRL 18539, or an A83543-producing mutant of NRRL 18395, NRRL 18537, NRRL 18538 or NRRL 18539. The purified cultures are useful for producing the A83543 components.

DESCRIPTION OF THE DRAWING

Infrared absorption spectra of A83543 components A and D and the pseudoaglycone of A83543A (in $CHCl_3$) are shown in FIGS. 1–3 and of components E, F, G and H/J (in KBr disk) are shown in FIGS. 13–16 as follows.

The field-desorption mass spectra (FD-MS) of A83543 components A, C and D and the pseudoaglycone of A83543A are shown in FIGS. 4–7 as follows:

FIG. 7—A83543A pseudoaglycone

Figure 9A:
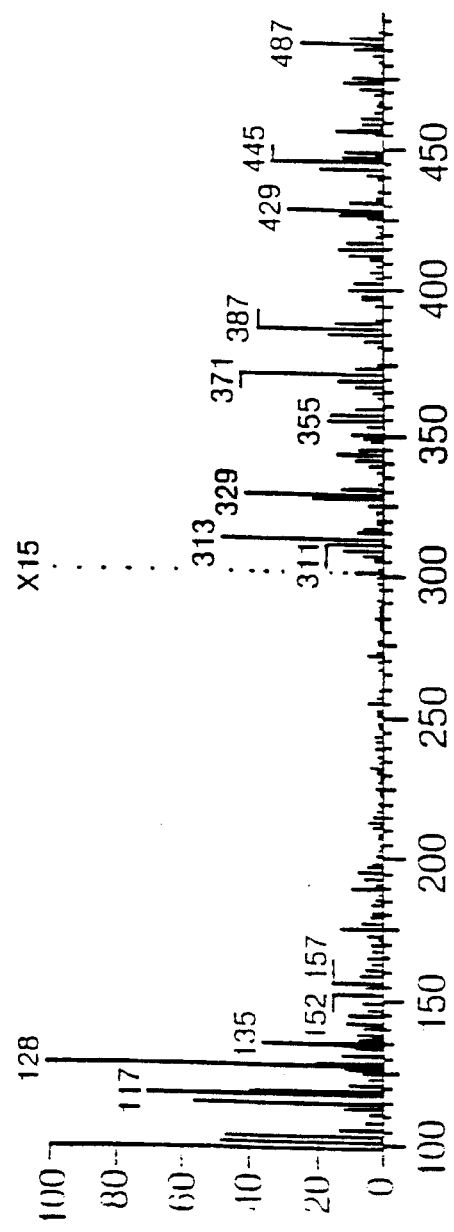
Figure 9B:

The fast-atom bombardment mass spectra (FAB-MS) of A83543 compounds A and B are shown in FIGS. 8–9 as follows [FAB dispersant—dithiothreitol:dithioerythritol (5:1)]:

FIG. 8—A83543A

FIG. 9—A83543B

Figure 10A:
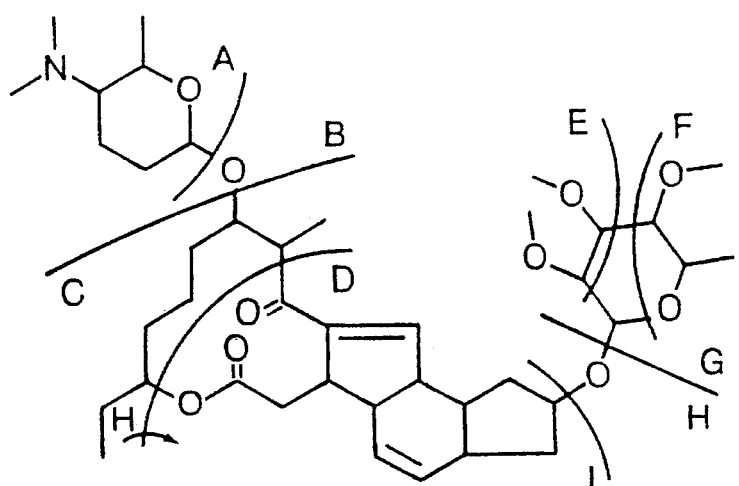
Figure 10B:
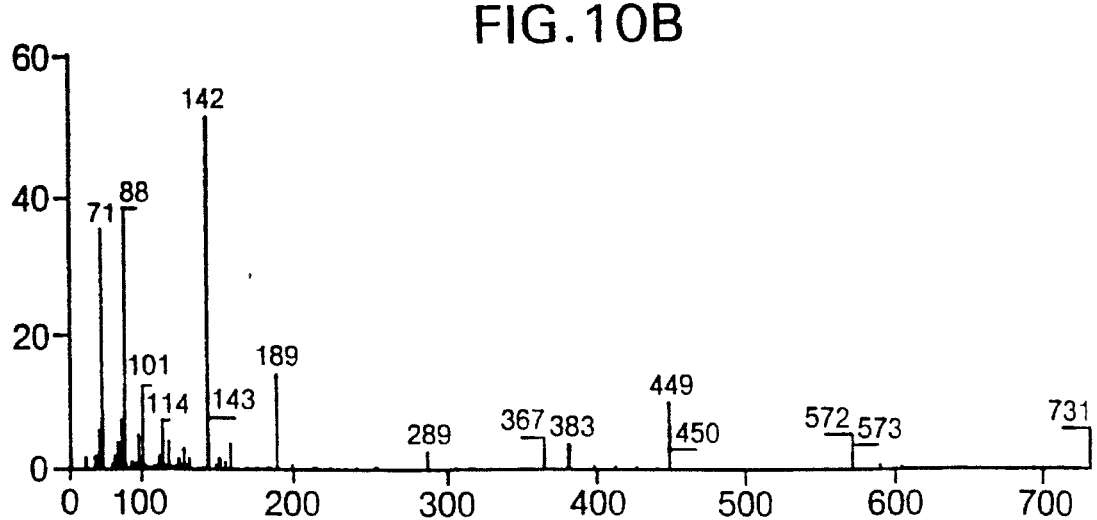
Figure 11A:
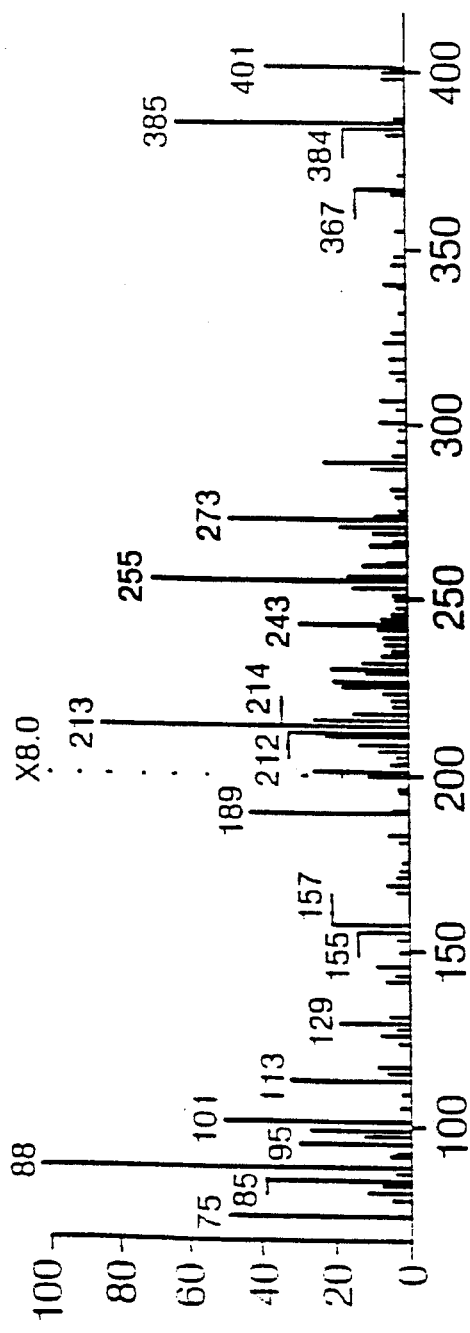
Figure 11B:
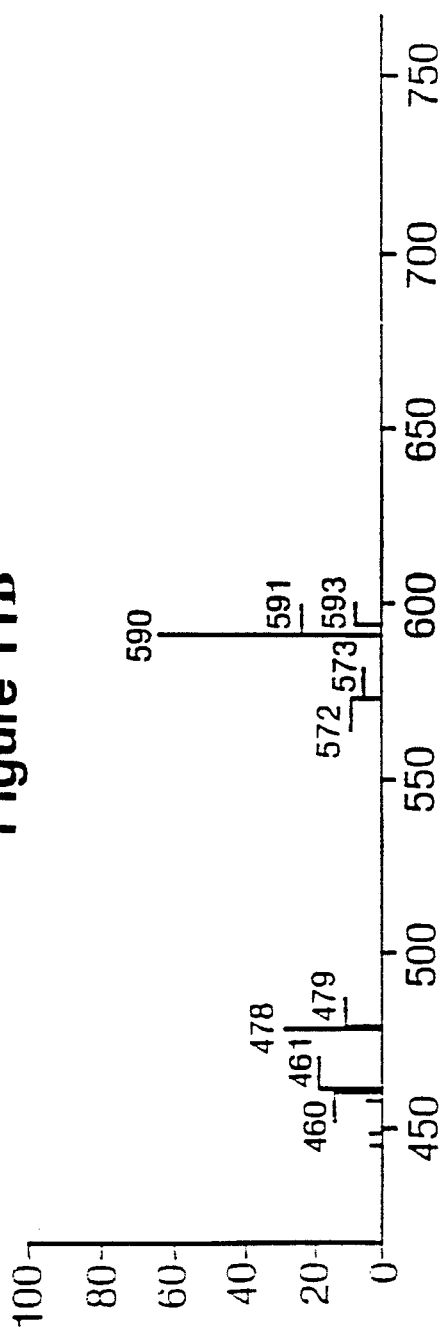

The electron-impact mass spectra (EI-MS) of A83543A and its pseudoaglycone are shown in FIGS. 10–11 as follows:

FIG. 10—A83543A

FIG. 11—A83543A pseudoaglycone

Figure 12:
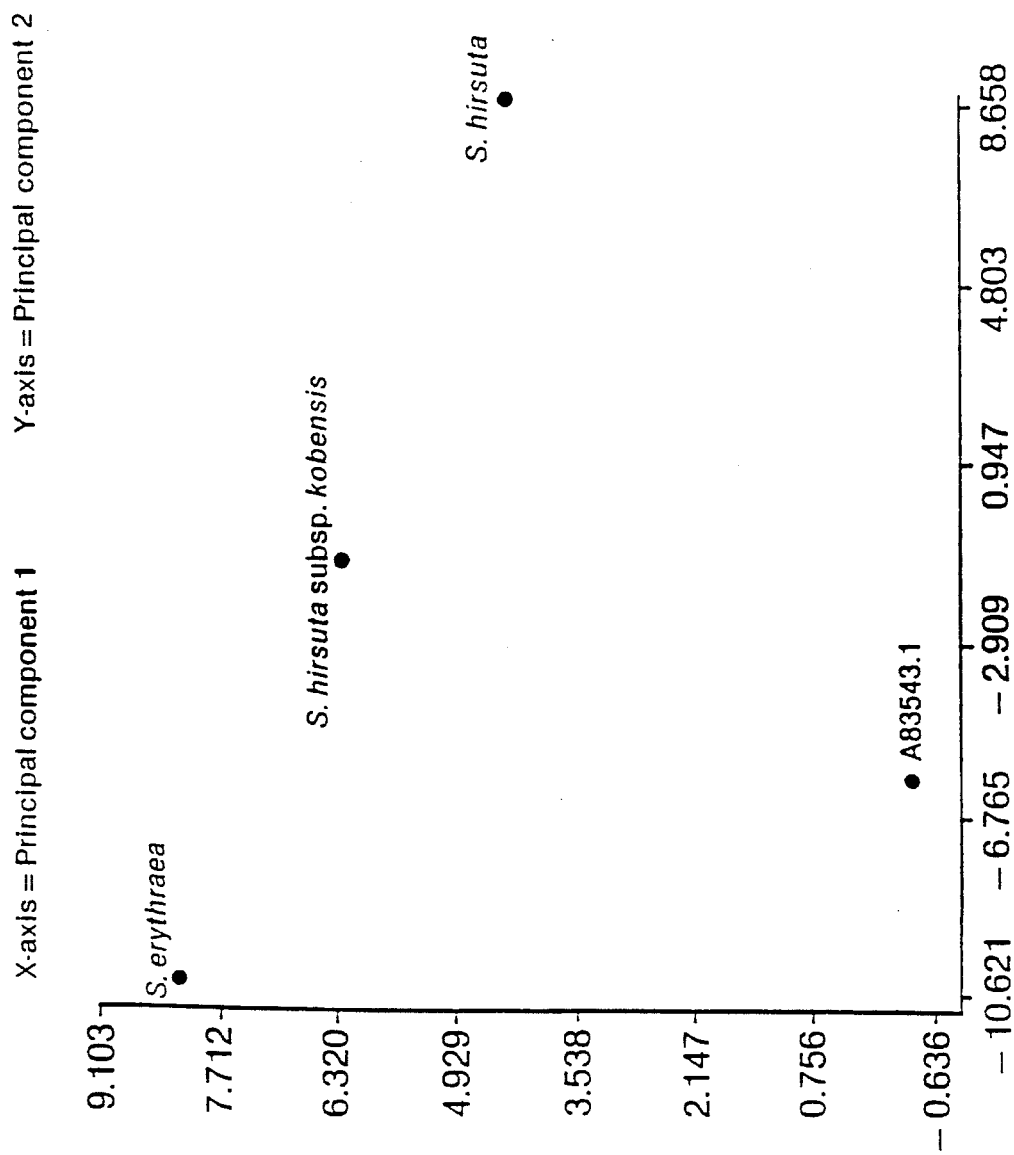

FIG. 12 is a principal component plot which compares the fatty acids present in culture A83543.1 with those of known *Saccharopolyspora* species.

DETAILED DESCRIPTION OF THE INVENTION

This invention relates to a new fermentation product which has been designated "A83543". A83543 is comprised of individual components A83543A, A83543B, A83543C, A83543D, A83543E, A83543F, A83543G, A83543H and A83543J. Further aspects of this invention are the individual A83543 components and their salts, especially their acid addition salts, and the pseudoaglycones of the A83543 components.

A83543 is produced by culturing a strain of the novel microorganism *Saccharopolyspora spinosa* selected from NRRL 18395, NRRL 18537, NRRL 18538 and NRRL 18539, or an A83543-producing mutant thereof. As those skilled in fermentation processes will recognize, the ratio of the components in A83543 will vary, depending upon the fermentation conditions used to produce it. In general, A83543 contains about 85–90% A83543A, about 10–15% A83543D and minor amounts of A83543B, C, E, F, G. H and J. Individual components A83543A, A83543B, A83543C, A83543D, A83543E, A83543F, A83543G, A83543H, and A83543J are separated and isolated, as described infra.

In discussion of utility, the term "A83543 compound" will denote a member selected from the group consisting of A83543, individual components A83543A, A83543B, A83543C, A83543D, A83543E, A83543F, A83543G, A83543H, and A83543J and their acid addition salts.

The compounds of this invention are compounds of formula 1:

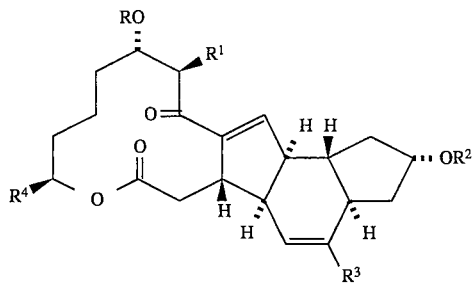

wherein
R is H or a group selected from

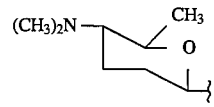 (a)

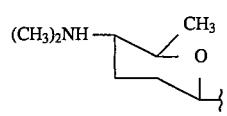 (b)

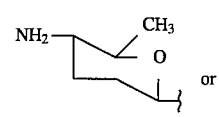 (c)

or

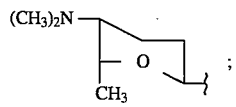 (d)

;

$R^2$ is

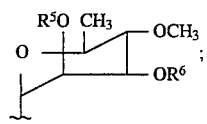 ;

$R^1$, $R^3$, $R^5$ and $R^6$ are hydrogen or methyl; and $R_4$ is methyl or ethyl;
provided that R, $R^1$, $R^3$, $R^4$, $R^5$ and $R^6$ must be present in one of the following combinations:

| R | $R_1$ | $R^3$ | $R^4$ | $R^5$ | $R^6$ |
|---|---|---|---|---|---|
| (a) | Me | H | Et | Me | Me |
| (b) | Me | H | Et | Me | Me |
| (c) | Me | H | Et | Me | Me |
| (a) | Me | Me | Et | Me | Me |
| (a) | Me | H | Me | Me | Me |

-continued

| R | $R_1$ | $R^3$ | $R^4$ | $R^5$ | $R^6$ |
|---|---|---|---|---|---|
| (a) | H | H | Et | Me | Me |
| (d) | Me | H | Et | Me | Me |
| (a) | Me | H | Et | H | Me |
| (a) | Me | H | Et | Me | H |
| H | Me | H | Et | Me | Me |
| H | Me | Me | Et | Me | Me |
| H | Me | H | Me | Me | Me |
| H | H | H | Et | Me | Me |
| H | Me | H | Et | H | Me |
| H | Me | H | Et | Me | H | and the acid addition salts of the compounds wherein R is other than hydrogen.

The aminosugar in A83543A has been shown to be β-D-forosamine; and the neutral sugar in A83543A is α-2, 3,4-tri-O-methylrhamnose.

Nine A83543 components have been characterized. These components are the formula 1 compounds wherein R is other than H. They have the following structures:

| Component | R | $R^1$ | $R^3$ | $R^4$ | $R^5$ | $R^6$ |
|---|---|---|---|---|---|---|
| A | (a) | Me | H | Et | Me | Me |
| B | (b) | Me | H | Et | Me | Me |
| C | (c) | Me | H | Et | Me | Me |
| D | (a) | Me | Me | Et | Me | Me |
| E | (a) | Me | H | Me | Me | Me |
| F | (a) | H | H | Et | Me | Me |
| G | (d) | Me | H | Et | Me | Me |
| H | (a) | Me | H | Et | H | Me |
| J | (a) | Me | H | Et | Me | H |

The amino sugar can be removed from the A83543 components to give pseudoaglycones (compounds of formula 1 where R=H). Components A, B, C and G have a common pseudoaglycone (the A83543A pseudoaglycone or pseudo-A). A83543A pseudoaglycone was later found to be produced naturally as an A83543 component. Components D, E, F, H and J each have a unique pseudoaglycone. The A83543 pseudoaglycones have the following structures:

| Pseudoaglycone[a] | $R^1$ | $R^3$ | $R^4$ | $R^5$ | $R^6$ |
|---|---|---|---|---|---|
| A83543A | Me | H | Et | Me | Me |
| A83543D | Me | Me | Et | Me | Me |
| A83543E | Me | H | Me | Me | Me |
| A83543F | H | H | Et | Me | Me |
| A83543H | Me | H | Et | H | Me |
| A83543J | Me | H | Et | Me | H |

[a] R = H

The pseudoaglycones are useful as intermediates, for example, to the A83543 components.

The following paragraphs describe the physical and spectral properties of the A83543 components and pseudoaglycones.

A83543A

A83543A has the following characteristics:

Molecular Weight: 731

Empirical Formula: $C_{41}H_{65}NO_{10}$

Figure 4:
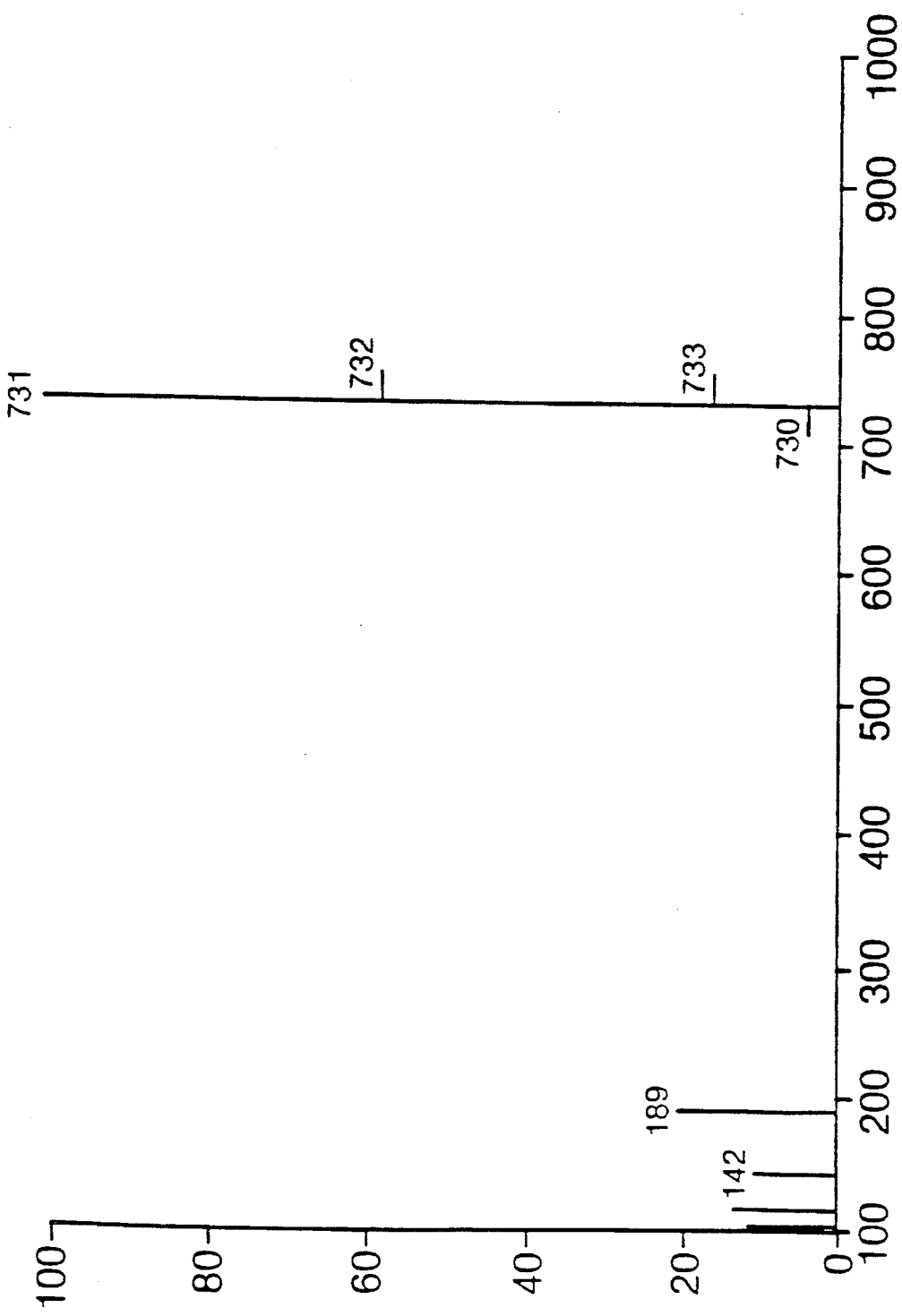
Figure 5:
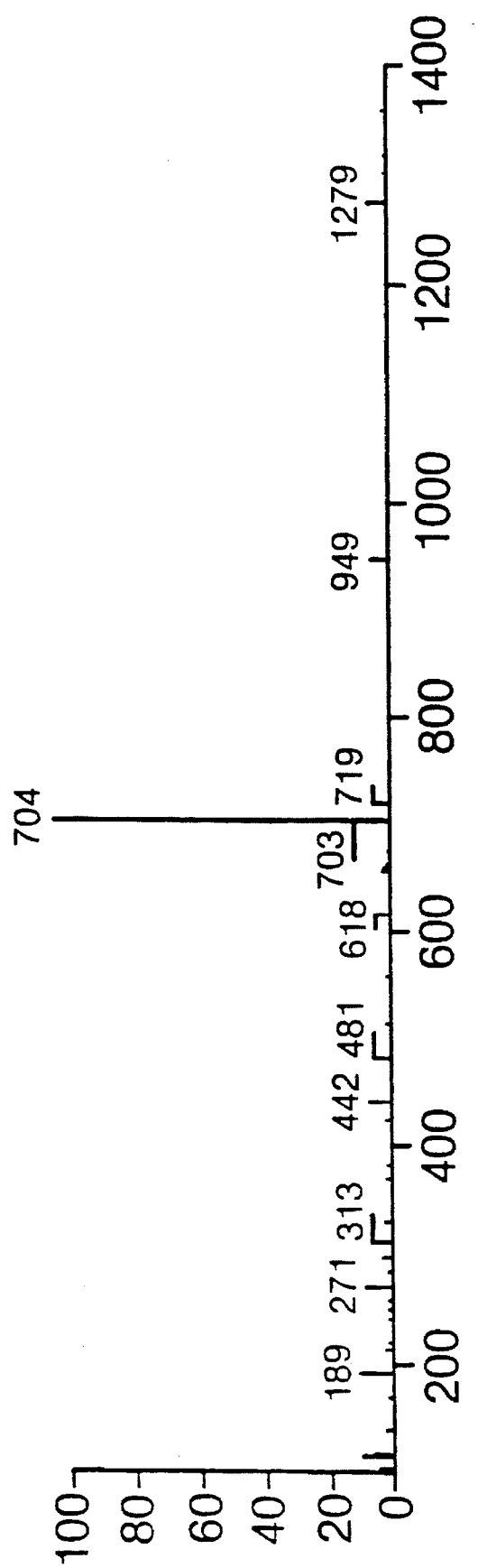

FD-MS: see FIG. 4

FAB-MS(M+1): Found: 732.4706; Calcd. $C_{41}H_{66}NO_{10}=$ 732.4687 (see FIG. 8)

EI-MS: Found: 731.4612; Calcd. 731.4608 (see FIG. 10)

Figure 1:
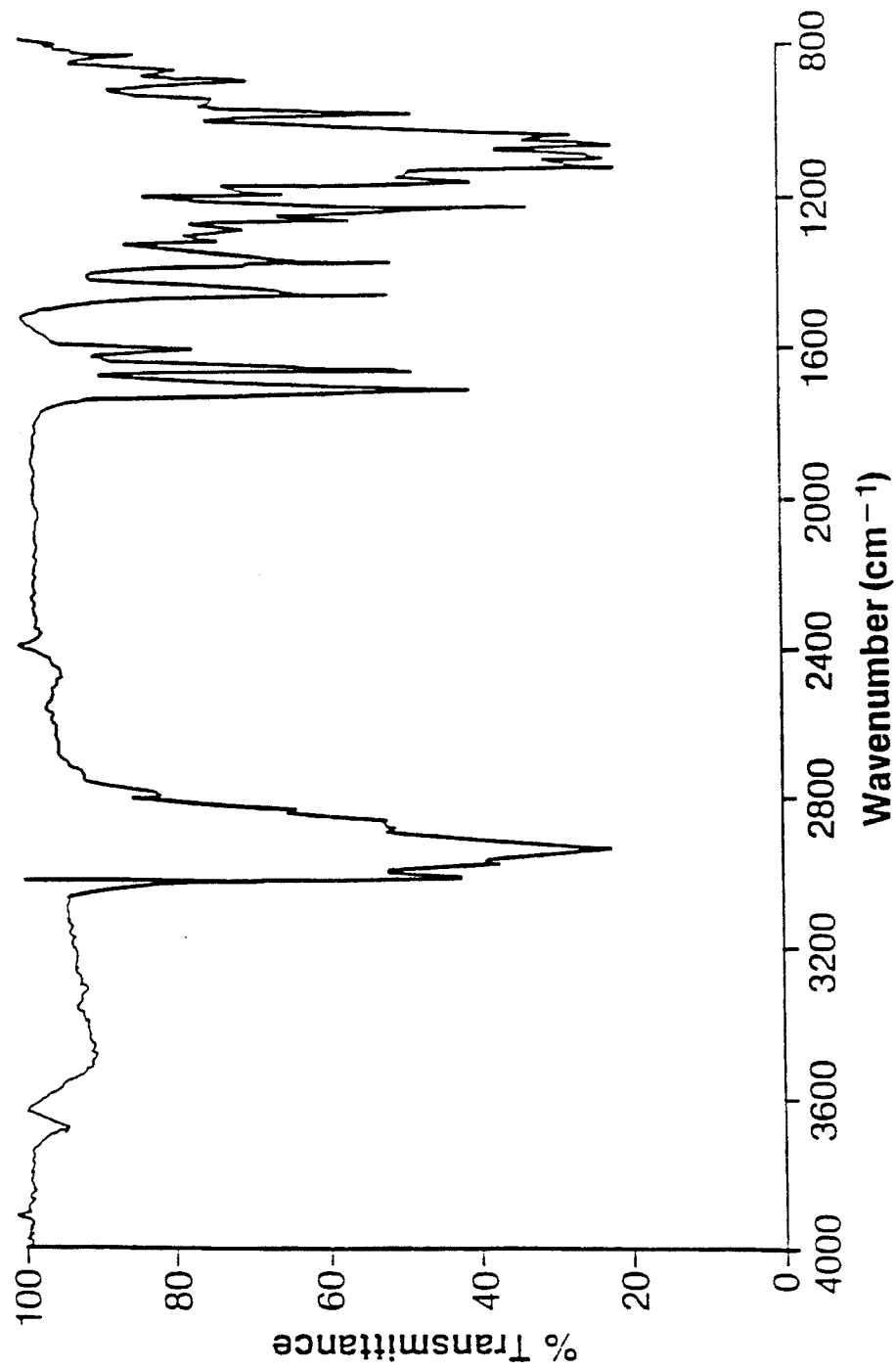
FIG. 1—A83543A

UV (EtOH) λmax: 243 nm (ε 8,920),
IR (CHCl$_3$): ν (lactone) 1713; (conjugated ketone) 1657; multiple peaks for C—H vibrations around 2940 and for C—O vibrations around 1060 cm$^{-1}$ (see FIG. 1)

$[\alpha]_D^{529}$: −121.8° (c 1.03, CHCl$_3$)

$[\alpha]_D^{365}$: +6.8° (c 1.03, CHCl$_3$)

Table I summarizes the $^1$H and $^{13}$C NMR data observed with A83543A (in acetone-d$_6$).

TABLE I $^1$H and $^{13}$C NMR Data of A83543A in Acetone-d$_6$.

| Position | $^{13}$C | $^1$H$^a$ |
| --- | --- | --- |
| 1 | 172.02 | — |
| 2 | 33.83 | 3.07/2.45 |
| 3 | 48.13 | 2.94 |
| 4 | 41.65 | 3.48 |
| 5 | 129.12 | 5.86 |
| 6 | 129.66 | 5.89 |
| 7 | 41.46 | 2.15 |
| 8 | 36.50 | 1.99/1.34 |
| 9 | 76.31$^+$ | 4.31 |
| 10 | 37.65 | 2.36/1.36 |
| 11 | 46.42 | 0.93 |
| 12 | 49.74 | 2.87 |
| 13 | 147.78 | 7.01 |
| 14 | 144.27 | — |
| 15 | 202.46 | — |
| 16 | 47.74 | 3.30 |
| 17 | 80.41 | 3.53 |
| 18 | 30.33 | 1.51 |
| 19 | 21.85 | 1.78/1.17 |
| 20 | 34.45 | 1.50 |
| 21 | 76.24$^+$ | 4.66 |
| 22 | 28.51 | 1.48 |
| 23 | 8.97 | 0.81 |
| 24 | 15.71 | 1.12 |
| 1' | 96.34 | 4.81 |
| 2' | 77.61 | 3.51 |
| 3' | 81.87 | 3.37 |
| 4' | 82.43 | 3.00 |
| 5' | 68.03 | 3.48 |
| 6' | 17.64 | 1.18 |
| 2'-OCH$_3$ | 56.66* | 3.37 |
| 3'-OCH$_3$ | 58.39* | 3.41 |
| 4'-OCH$_3$ | 60.12 | 3.45 |
| 1" | 103.45 | 4.45 |
| 2" | 31.24 | 1.92/1.37 |
| 3" | 18.14 | 1.84/1.52 |
| 4" | 65.34 | 2.12 |
| 5" | 73.35 | 3.56 |
| 6" | 18.87 | 1.21 |
| N(CH$_3$)$_2$ | 40.38 | 2.22 |

$^a$Some measurements were taken from $^1$H/$^{13}$C correlation.
$^+$,*Resonances with the same superscript may be interchanged.

A83543B

A83543B has the following characteristics:

Molecular Weight: 717

Empirical Formula: C$_{40}$H$_{63}$NO$_{10}$

FAB-MS: (see FIG. 9)

A83543C

A83543C has the following characteristics:

Molecular Weight: 703

Empirical Formula: C$_{39}$H$_{61}$NO$_{10}$

FD-MS: (see FIG. 5)

A83543D

A83543D has the following characteristics:

Molecular Weight: 745

Empirical Formula: C$_{42}$H$_{67}$NO$_{10}$

UV (EtOH) λmax: 244 nm (ε 9,910)

Figure 2:
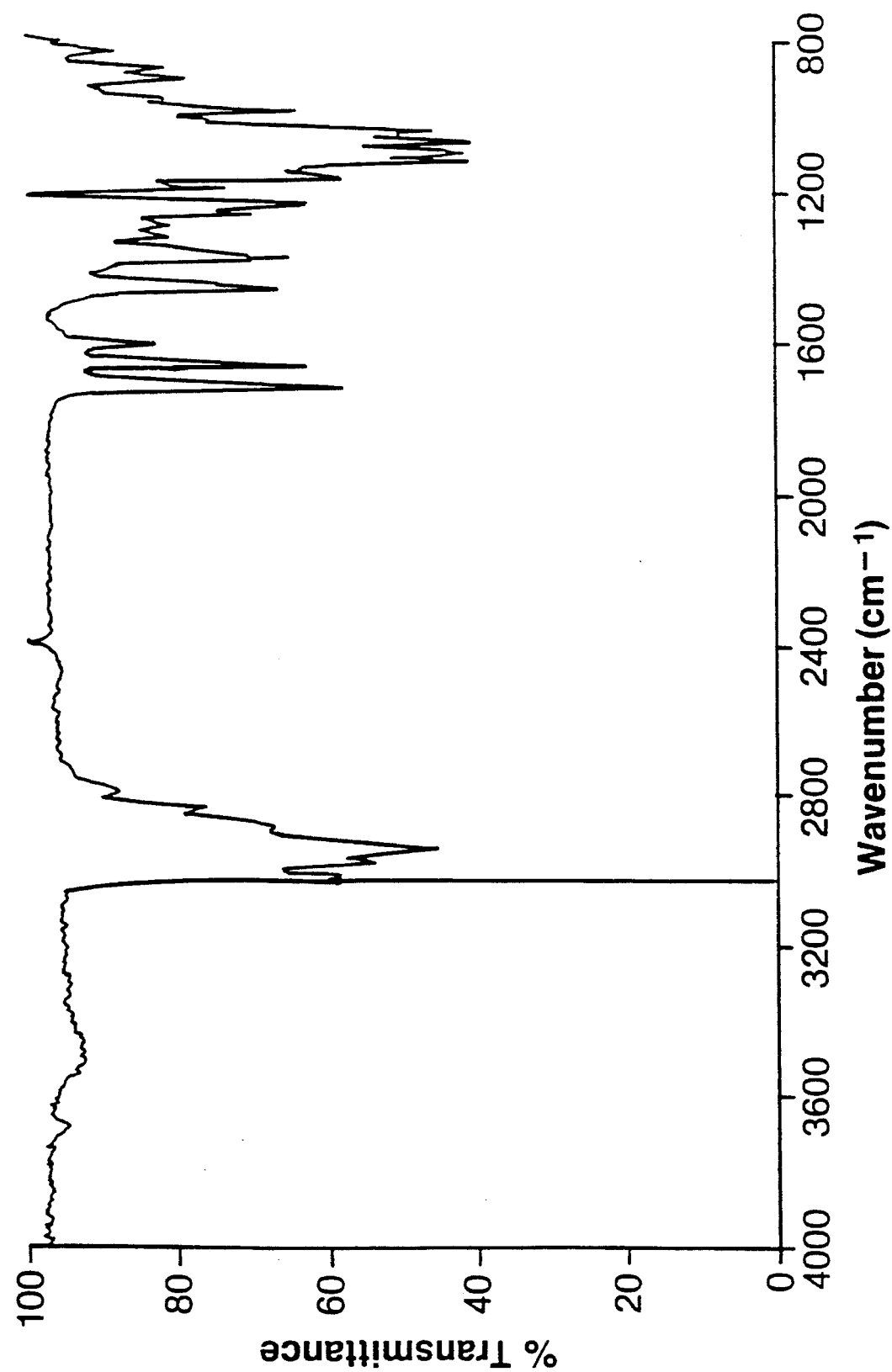
FIG. 2—A83543D

IR (CHCl$_3$): ν (lactone) 1708; (conjugated ketone) 1658; multiple peaks for C—H vibrations around 2940 and for C—O vibrations around 1070 cm$^{-1}$ (see FIG. 2)

$[\alpha]_D^{389}$: −142.9° (c 1.02, CHCl$_3$)

$[\alpha]_D^{365}$: −29.9° (c 1.02, CHCl$_3$)

FD-MS: see FIG. 6

Table II summarizes the $^1$H and $^{13}$C NMR data observed with A83543D (in acetone-d$_6$).

TABLE II $^1$H and $^{13}$C NMR Data of A83543D in Acetone-d$_6$.

| Position | $^{13}$C | $^1$H$^a$ |
| --- | --- | --- |
| 1 | 172.68 | — |
| 2 | 34.38 | 3.08/2.43 |
| 3 | 49.01 | 2.90 |
| 4 | 42.83 | 3.47 |
| 5 | 123.27 | 5.54 |
| 6 | 137.26 | — |
| 6-CH$_3$ | 20.81 | 1.74 |
| 7 | 44.41 | 2.18 |
| 8 | 35.61 | 2.01/1.45 |
| 9 | 76.72 | 4.32 |
| 10 | 38.64 | 2.37/1.37 |
| 11 | 47.04 | 1.02 |
| 12 | 50.05 | 2.78 |
| 13 | 148.47 | 7.04 |
| 14 | 145.19 | — |
| 15 | 203.16 | — |
| 16 | 48.47 | 3.30 |
| 17 | 81.03 | 3.53 |
| 18 | 30.99 | 1.49 |
| 19 | 22.51 | 1.78/1.19 |
| 20 | 35.12 | 1.49 |
| 21 | 76.84 | 4.65 |
| 22 | 29.16 | 1.48 |
| 23 | 9.55 | 0.81 |
| 24 | 16.32 | 1.12 |
| 1' | 97.11 | 4.85 |
| 2' | 78.33 | 3.54 |
| 3' | 82.58 | 3.40 |
| 4' | 83.15 | 3.03 |
| 5' | 68.71 | 3.50 |
| 6' | 18.26 | 1.18 |
| 2'-OCH$_3$ | 57.31* | 3.40 |
| 3'-OCH$_3$ | 59.02* | 3.43 |
| 4'-OCH$_3$ | 60.71 | 3.47 |
| 1" | 104.14 | 4.47 |
| 2" | 31.96 | 1.94/1.39 |
| 3" | 18.83 | 1.81/1.49 |
| 4" | 66.06 | 2.12 |
| 5" | 74.12 | 3.55 |
| 6" | 19.42 | 1.20 |
| N(CH$_3$)$_2$ | 40.99 | 2.21 |

$^a$Some assignments taken from $^1$H/$^{13}$C correlation.
*Resonances may be interchanged.

A83543E

A83543E has the following characteristics:

Molecular Weight: 717

Empirical Formula: C$_{40}$H$_{63}$NO$_{10}$

FAB-MS (M+1): Found: 718.4526; Calcd. C$_{40}$H$_{64}$NO$_{10}$= 718.4530

UV (EtOH) λmax: 244 nm (ε 8,600)

Figure 13:
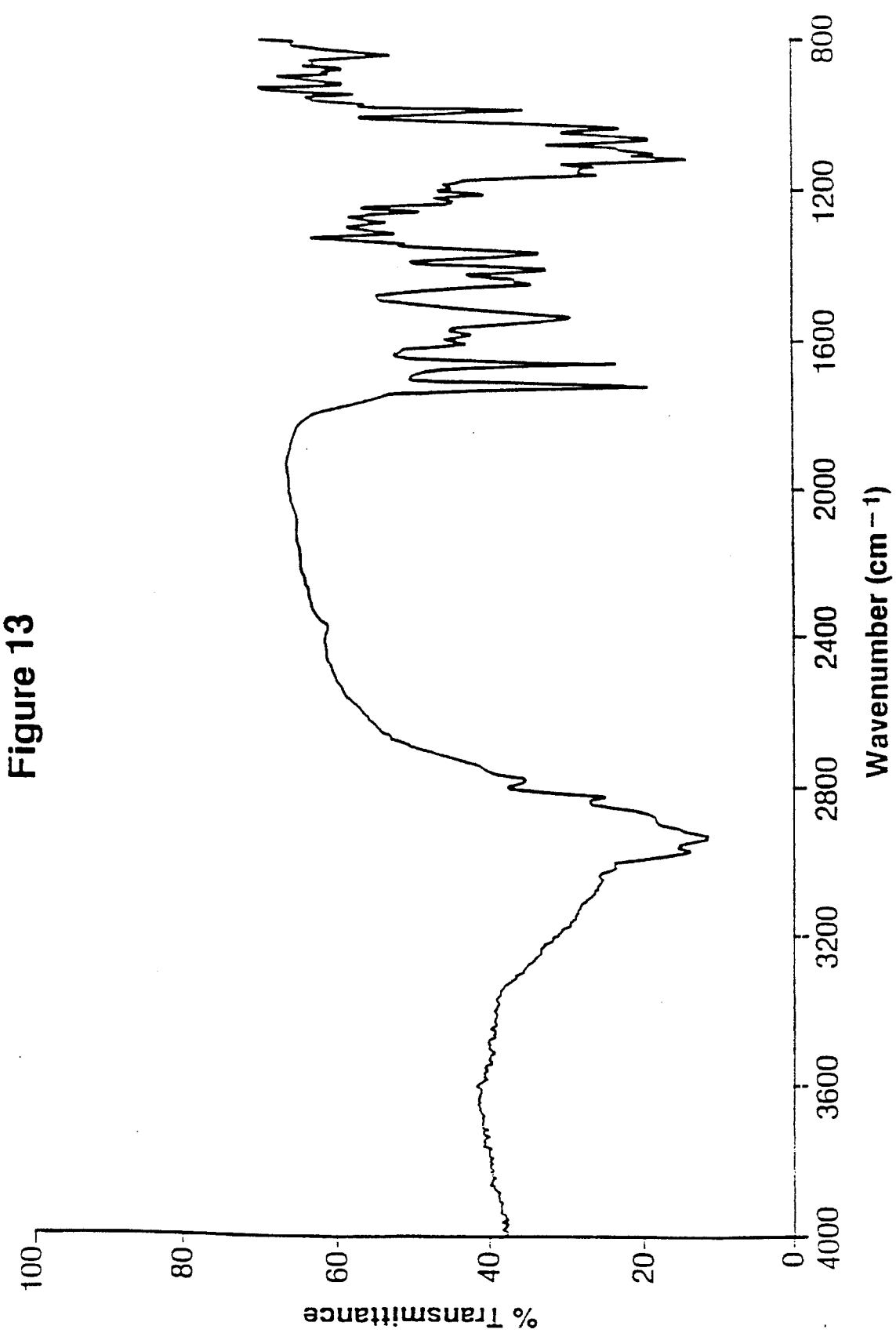
FIG. 13—A83543E

IR (KBr) (see FIG. 13)

Table III summarizes the $^1$H and $^{13}$C NMR data observed with A83543E (in acetone-d$_6$).

TABLE III

$^1$H and $^{13}$C NMR Data of A83543E in Acetone-$d_6$.

| Position | $^{13}$C | $^1$H$^a$ |
|---|---|---|
| 1 | 172.46 | — |
| 2 | 34.95 | 3.06/2.40 |
| 3 | 48.88 | 2.95 |
| 4 | 42.11 | 3.43 |
| 5 | 129.78 | 5.86 |
| 6 | 130.39 | 5.90 |
| 7 | 42.11 | 2.14 |
| 8 | 37.18 | 1.96/1.39 |
| 9 | 77.06 | 4.33 |
| 10 | 38.31 | 2.36/1.36 |
| 11 | 47.18 | 0.93 |
| 12 | 50.40 | 2.86 |
| 13 | 148.37 | 7.06 |
| 14 | 144.84 | — |
| 15 | 203.09 | — |
| 16 | 48.05 | 3.34 |
| 17 | 81.35 | 3.55 |
| 18 | 34.98 | 1.62/1.48 |
| 19 | 22.25 | 1.77/1.13 |
| 20 | 33.73 | 1.50 |
| 21 | 72.97 | 4.68 |
| 22 | 21.61 | 1.12 |
| 23 | — | — |
| 24 | 16.52 | 1.13 |
| 1' | 97.11 | 4.83 |
| 2' | 78.36 | 3.55 |
| 3' | 82.55 | 3.37 |
| 4' | 83.13 | 3.02 |
| 5' | 68.72 | 3.50 |
| 6' | 18.26 | 1.18 |
| 2'-OCH$_3$ | 59.01 | 3.43 |
| 3'-OCH$_3$ | 57.30 | 3.40 |
| 4'-OCH$_3$ | 60.69 | 3.46 |
| 1" | 104.24 | 4.47 |
| 2" | 32.00 | 1.93/1.39 |
| 3" | 18.86 | 1.82/1.50 |
| 4" | 66.06 | 2.12 |
| 5" | 74.13 | 3.57 |
| 6" | 19.42 | 1.21 |
| N(CH$_3$)$_2$ | 40.99 | 2.21 |

$^a$Some measurements were taken from $^1$H/$^{13}$C correlation.

A83543F

A83543F has the following characteristics:

Molecular Weight: 717

Empirical Formula: $C_{40}H_{63}NO_{10}$

FAB-MS (M+1): Found: 718.4534; Calcd. $C_{40}H_{64}NO_{10}$= 718.4530

UV (EtOH) $\lambda$max: 243 nm ($\epsilon$ 10,500) and 282 nm ($\epsilon$ 109)

Figure 14:
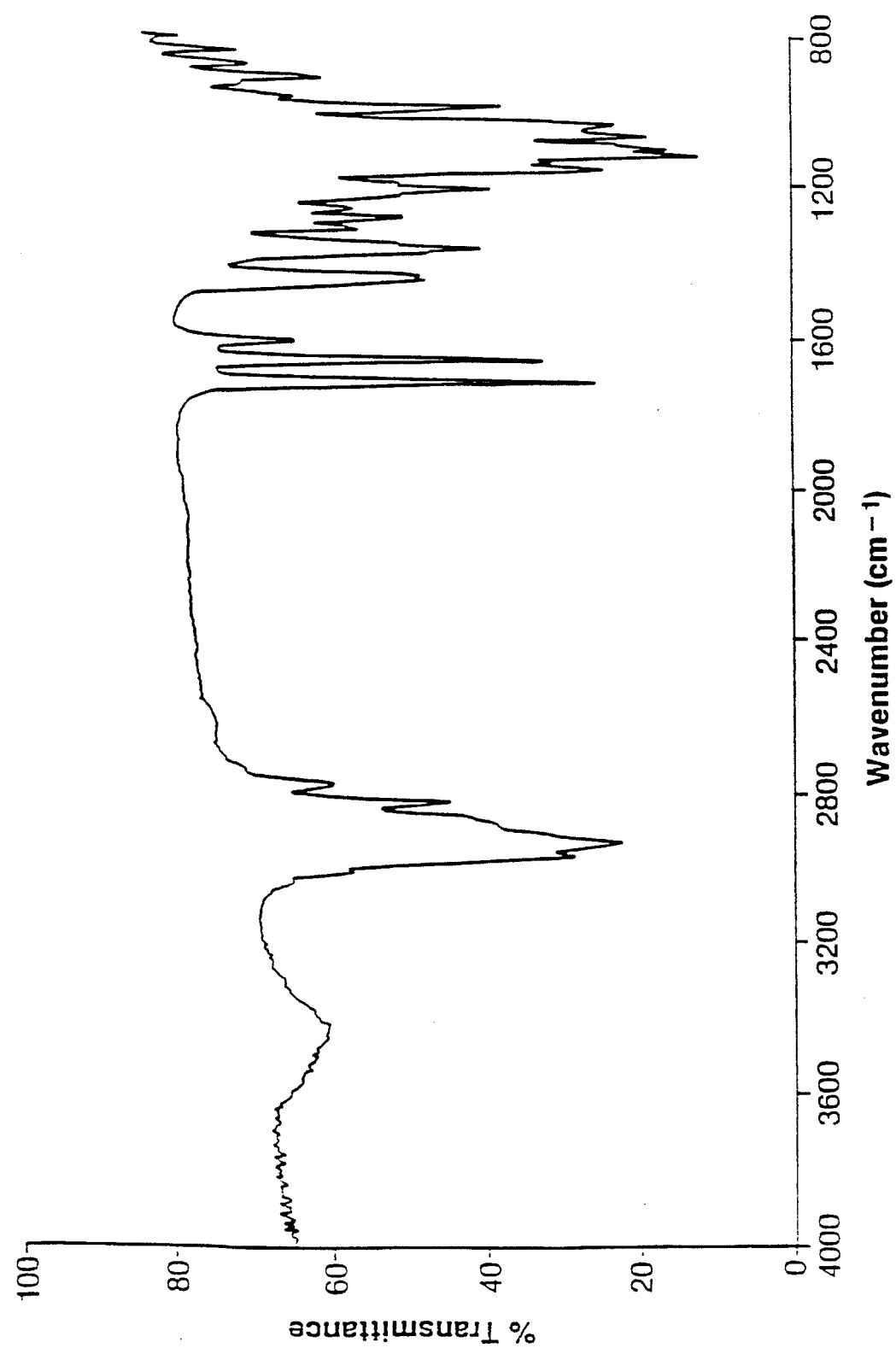
FIG. 14—A83543F

IR (KBr): (see FIG. 14)

Table IV summarizes the $^1$H and $^{13}$C NMR data observed with A83543F (in acetone-$d_6$).

TABLE IV

$^1$H and $^{13}$C NMR Data of A83543F in Acetone-$d_6$.

| Position | $^{13}$C | $^1$H$^a$ |
|---|---|---|
| 1 | 172.60 | — |
| 2 | 34.50 | 3.06/2.42 |
| 3 | 48.82 | 2.95 |
| 4 | 42.46 | 3.45 |
| 5 | 129.56 | 5.87 |
| 6 | 130.39 | 5.92 |
| 7 | 42.19 | 2.16 |
| 8 | 37.18 | 1.97/1.35 |
| 9 | 77.15 | 4.65 |
| 10 | 38.30 | 2.33/1.34 |
| 11 | 46.89 | 0.94 |
| 12 | 50.34 | 2.84 |
| 13 | 148.86 | 7.03 |
| 14 | 145.73 | — |
| 15 | 198.68 | — |
| 16 | 45.49 | 3.22/2.50 |
| 17 | 74.17 | 3.58 |
| 18 | 30.74 | 1.52 |
| 19 | 22.41 | 1.70/1.17 |
| 20 | 34.45 | 1.51 |
| 21 | 77.09 | 4.32 |
| 22 | 29.05 | 1.48 |
| 23 | 9.56 | 0.81 |
| 1' | 97.19 | 4.83 |
| 2' | 78.38 | 3.53 |
| 3' | 82.58 | 3.38 |
| 4' | 83.15 | 3.00 |
| 5' | 68.74 | 3.48 |
| 6' | 18.25 | 1.18 |
| 2'-OCH$_3$ | 59.02 | 3.43 |
| 3'-OCH$_3$ | 57.31 | 3.40 |
| 4'-OCH$_3$ | 60.69 | 3.47 |
| 1" | 100.19 | 4.53 |
| 2" | 32.41 | 1.80/1.38 |
| 3" | 18.86 | 1.83/1.53 |
| 4" | 66.16 | 2.13 |
| 5" | 74.01 | 4.01 |
| 6" | 19.46 | 1.22 |
| N(CH$_3$)$_2$ | 41.01 | 2.22 |

$^a$Some measurements were taken from $^1$H/$^{13}$C correlation.

A83543G

A83543G has the following characteristics:

Molecular Weight: 731

Empirical Formula: $C_{41}H_{65}NO_{10}$

FAB-MS (M+1): Found: 732.4661; Calcd. $C_{41}H_{66}NO_{10}$= 732.4687

UV (EtOH) $\lambda$max: 243 nm ($\epsilon$ 8.970)

Figure 15:
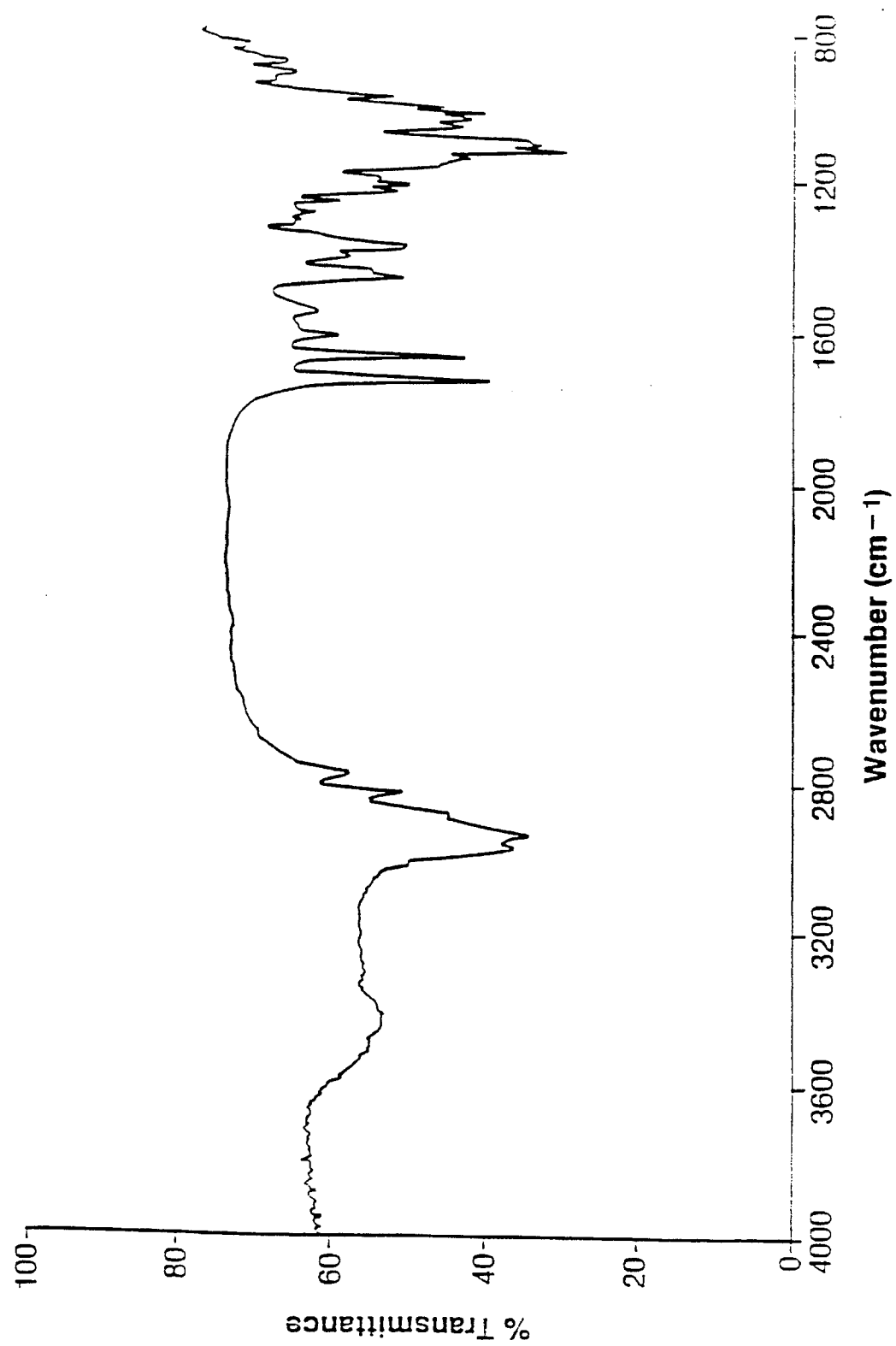
FIG. 15—A83543G

IR (KBr): (see FIG. 15)

Table V summarizes the $^1$H and $^{13}$C NMR data observed with A83543G (in acetone-$d_6$).

TABLE V

$^1$H and $^{13}$C NMR Data of A83543 in Acetone-$d_6$.

| Position | $^{13}$C | $^1$H$^a$ |
|---|---|---|
| 1 | 172.59 | — |
| 2 | 34.67 | 3.04/2.46 |
| 3 | 48.72 | 2.94 |
| 4 | 42.25 | 3.50 |
| 5 | 129.85 | 5.84 |
| 6 | 130.26 | 5.89 |
| 7 | 42.02 | 2.14 |
| 8 | 37.12 | 1.95/1.34 |
| 9 | 76.99 | 4.32 |
| 10 | 38.28 | 2.36/1.36 |
| 11 | 47.23 | 0.91 |
| 12 | 50.43 | 2.87 |
| 13 | 148.28 | 7.04 |
| 14 | 144.61 | — |
| 15 | 203.20 | — |
| 16 | 47.94 | 3.30 |
| 17 | 81.73 | 3.57 |
| 18 | 35.20 | 1.55 |
| 19 | 21.68 | 1.64/1.16 |
| 20 | 31.41 | 1.64/1.36 |
| 21 | 76.47 | 4.64 |

TABLE V-continued

$^1$H and $^{13}$C NMR Data of A83543 in Acetone-$d_6$.

| Position | $^{13}$C | $^1$H$^a$ |
|---|---|---|
| 22 | 28.84 | 1.48 |
| 23 | 9.61 | 0.80 |
| 24 | 15.29 | 1.18 |
| 1' | 96.98 | 4.81 |
| 2' | 78.23 | 3.52 |
| 3' | 82.46 | 3.37 |
| 4' | 83.05 | 2.29 |
| 5' | 68.64 | 3.49 |
| 6' | 17.18 | 1.12 |
| 2'-OCH$_3$ | 58.97 | 3.42 |
| 3'-OCH$_3$ | 57.25 | 3.39 |
| 4'-OCH$_3$ | 60.70 | 3.46 |
| 1" | 99.51 | 4.80 |
| 2" | 29.62 | 1.87/1.48 |
| 3" | 19.31 | 1.73 |
| 4" | 62.13 | 2.29 |
| 5" | 69.93 | 4.20 |
| 6" | 18.22 | 1.17 |
| N(CH$_3$)$_2$ | 43.47 | 2.24 |

$^a$Some measurements were taken from $^1$H/$^{13}$C correlation.

A83543H

A83543H has the following characteristics:

Molecular Weight: 717

Empirical Formula: $C_{40}H_{63}NO_{10}$

UV (EtOH) λmax: 243 nm (ε 10,100)*

Figure 16:
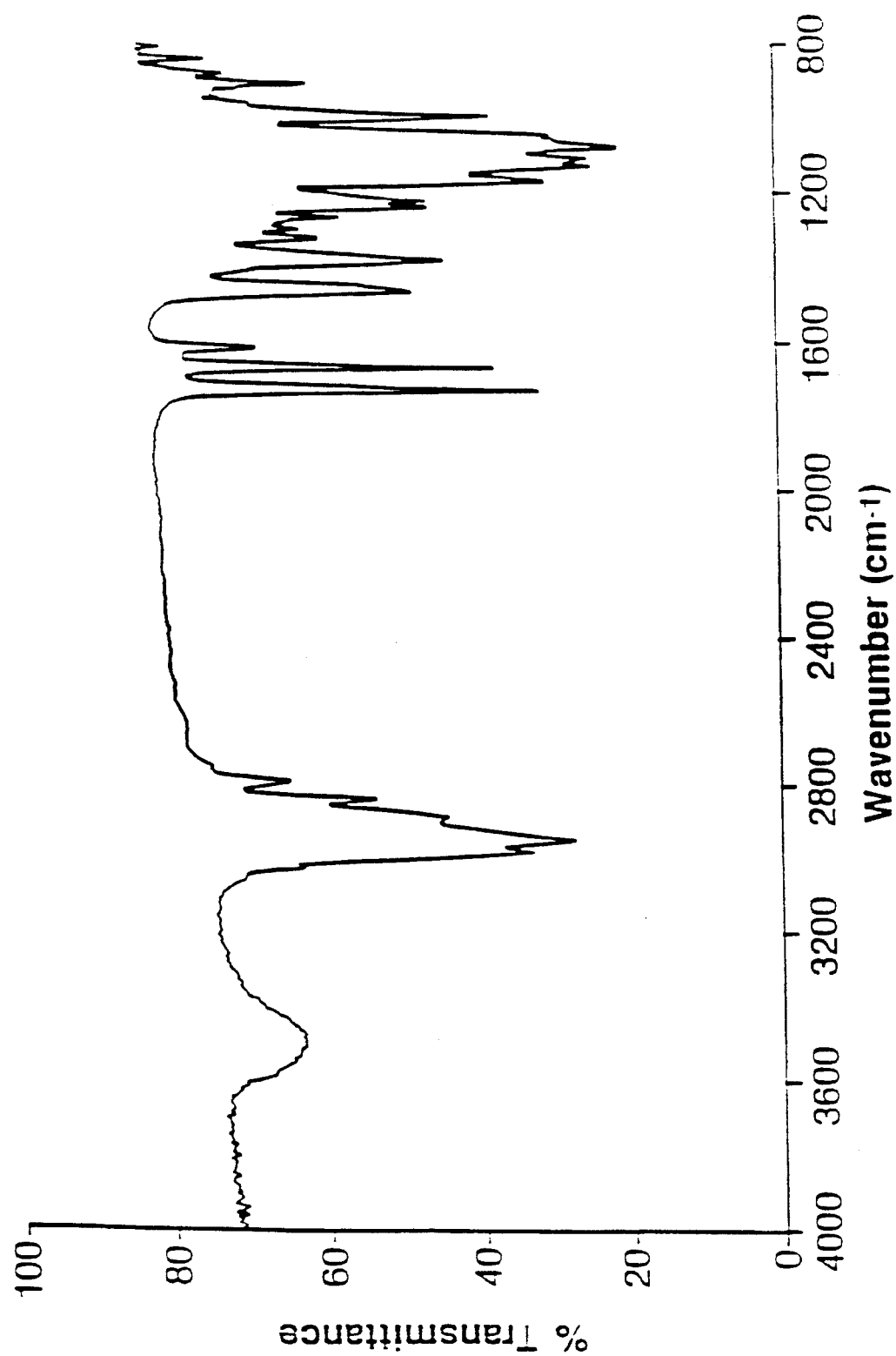
FIG. 16—A83543 H:J (58:42 mixture)
Figure 17:
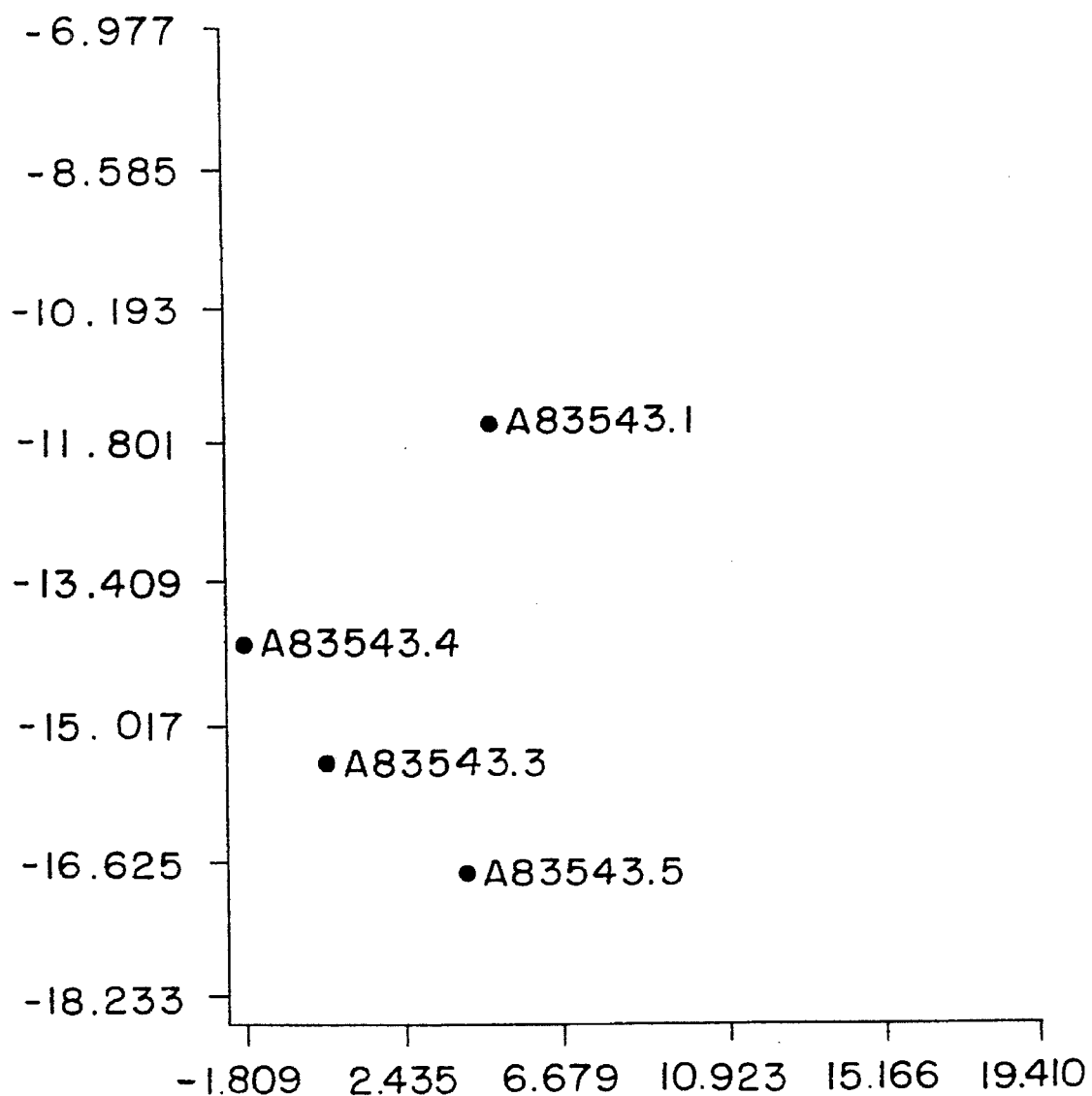

IR (KBr): see FIG. 16\*

* determined on an A83543H:J (58:42) mixture

A83543J

A83543J has the following characteristics:

Molecular Weight: 717

Empirical Formula: $C_{40}H_{63}NO_{10}$

UV (EtOH) λmax: 243 nm (ε 10,100)*

IR (CHCl$_3$): see FIG. 16\*

* determined on an A83543 H:J (58:42) mixture

A83543H and J are separated from A83543 as a mixture (H:J ratio=58:42) which can be separated by analytical high performance liquid chromatography (HPLC), as described infra. The structures assigned to A83543H and J are based on $^1$H and $^{13}$C NMR studies of the A83543 H:J mixture in acetone-$d_6$. The NMR spectra resemble and were compared with those of A83543A. The major changes in the H and J spectra center around the rhamnose sugar. Components H and J have only two OCH$_3$'s in that sugar. In component H, H1' is shifted about 0.1 δ in the $^1$H NMR spectrum and 3 δ in the $^{13}$C NMR spectrum (4.81 and 99.68, respectively). These shifts are due to the absence of methyl on the methoxy at the 2' position. The shifts in component J correspond to a similar absence of the methyl on the methoxy at the 3' position.

A83543A Pseudoaglycone

A83543A pseudoaglycone has the following characteristics:

Molecular Weight: 590

Empirical Formula: $C_{33}H_{50}O_9$

UV (EtOH) λmax: 243 nm (ε 10,300)

Figure 3:
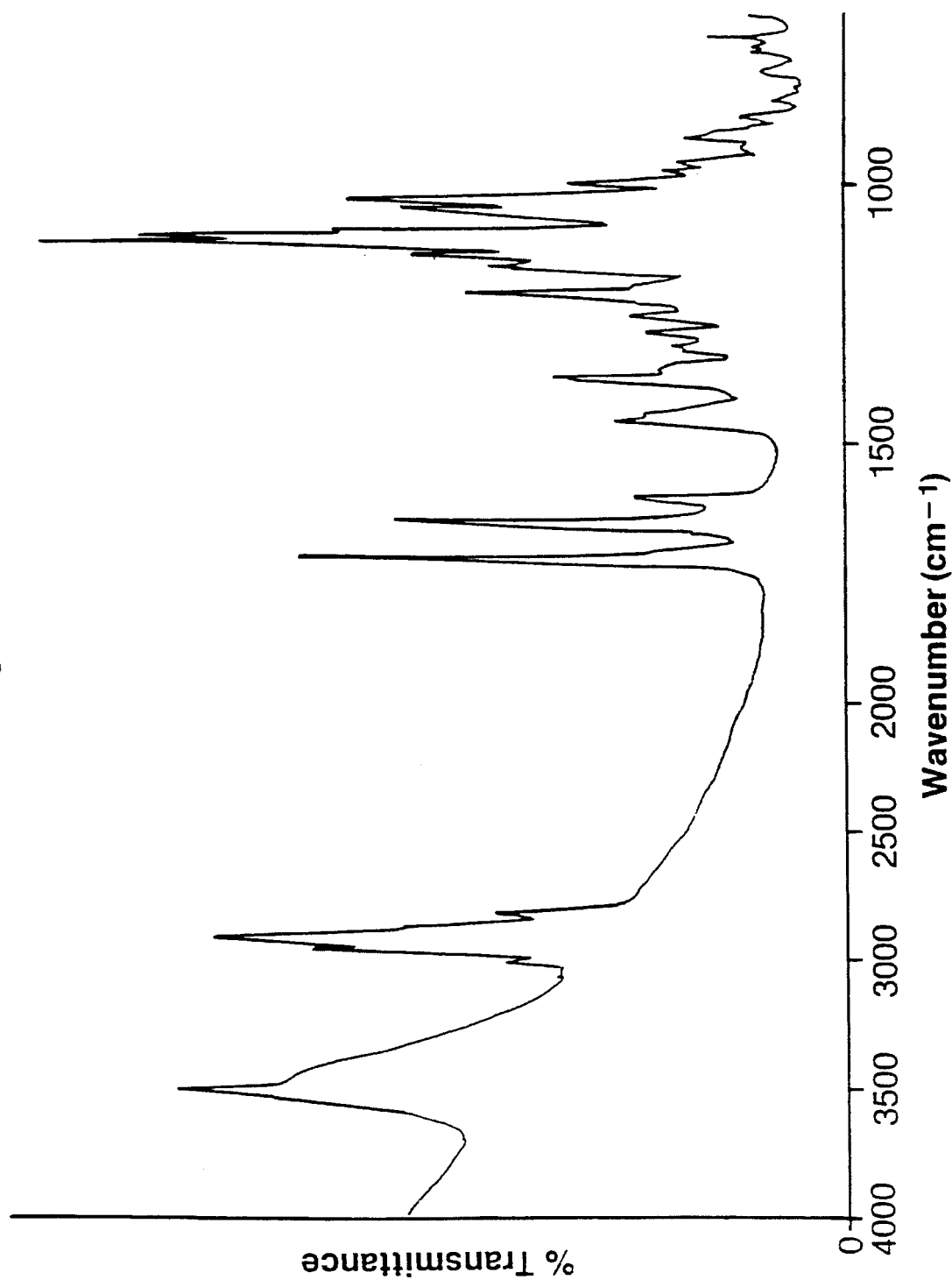
FIG. 3—A83543A pseudoaglycone

IR (CHCl$_3$): ν (lactone) 1724; (conjugated ketone 1652; multiple peaks for C—H vibrations around 3017; multiple peaks for C—O vibrations around 1140 cm$^{-1}$ (see FIG. 3)

FD-MS: see FIG. 7

EI-MS: see FIG. 11

A83543D Pseudoaglycone

A83543D pseudoaglycone has the following characteristics:

Molecular Weight: 604

Empirical Formula: $C_{34}H_{52}O_9$

The A83543 components can be separated from each other using one of the following analytical HPLC system:

SYSTEM I

Column: ODS, 3μ, 4.5×50 mm (IBM)
Solvent: CH$_3$OH:CH$_3$CN:H$_2$O (2:2:1)
Flow Rate: 1.0 mL/min
Detection: UV at 245 nm
Temperature: Room Temperature

| Component | Retention Time (min) |
|---|---|
| A | 8.50 |
| B | 6.15 |
| C | 3.92 |
| D | 11.47 |

SYSTEM II

Column: 4.6×100 mm, ODS
   (AQ-301, S-5; YMC, Inc., Mt. Freedom, N.J.)
Solvents: CH$_3$OH:CH$_3$CN:0.05% NH$_4$OAc(H$_2$O)
   (A) 35:35:30—pH 7.8
   (B) 45:45:10—pH 6.7
Flow Rate: 2.0 mL/min
Run time: 35 min
Detection: UV, 250 nm
Gradient: 10% B to 25% B in 20 min; to 50% B in 30 min

| Component | Retention Time (min) |
|---|---|
| A | 22.62 |
| A-pseudoaglycone | 7.27 |
| B | 12.65 |
| C | 10.62 |
| D | 25.47 |
| E | 19.22 |
| F | 16.30 |
| G | 18.92 |
| H | 16.30 |
| J | 17.50 |

SYSTEM III

Column: 4.6×100 mm, ODS
   (AQ-301, S-5; YMC, Inc., Mt. Freedom, N.J.)
Solvents: CH$_3$OH:CH$_3$CN:0.05% NH$_4$OAc(H$_2$O)
   35:35:30—pH 6.0
Flow Rate: 2.0 mL/min
Run time: 10 min Detection: UV, 250 nm

| Component | Retention Time (min) |
|---|---|
| F | 4.32 |
| H | 3.42 |
| J | 3.42 |

The A83543 components are not soluble in water, but are soluble in solvents such as methanol, ethanol, dimethylformamide, dimethyl sulfoxide, acetonitrile, acetone and the like.

A83543 and individual components A83543A, A83543B, A83543C, A83543D, A83543E, A83543F, A83543G, A83543H, and A83543J can react to form various salts. All such forms of these compounds are part of this invention. A83543 salts are useful, for example, for separating and purifying A83543. In addition, some salts have an improved solubility in water.

A83543 salts are prepared using standard procedures for salt preparation. For example, A83543 can be neutralized with an appropriate acid to form an acid addition salt.

The acid addition salts are particularly useful. Representative suitable salts include those salts formed by standard reactions with both organic and inorganic acids such as, for example, sulfuric, hydrochloric, phosphoric, acetic, succinic, citric, lactic, maleic, fumaric, cholic, pamoic, mucic, glutamic, camphoric, glutaric, glycolic, phthalic, tartaric, formic, lauric, stearic, salicylic, methanesulfonic, benzenesulfonic, sorbic, picric, benzoic, cinnamic and like acids.

A83543 is produced by culturing an A83543-producing strain of *Saccharopolyspora spinosa* sp. nov. under submerged aerobic conditions in a suitable culture medium until a recoverable amount of A83543 is produced. A83543 can be recovered using various isolation and purification procedures understood in the art.

This invention also relates to a biologically purified culture of the microorganism *Saccharopolyspora spinosa* selected from NRRL 18395, NRRL 18537, NRRL 18538 or NRRL 18539, or an A83543-producing mutant thereof. These microorganisms are useful because they produce A83543.

For convenience in the discussions which follow, the strains have been given the following designations: A83543.1, A83543.3, A83543.4 and A83543.5. Culture A83543.1 was obtained by chemical mutation of a culture (A83543) isolated from a soil sample collected from the Virgin Islands. Cultures A83543.3, A83543.4 and A83543.5 were obtained from derivatives of the A83543.1 culture by chemical mutations.

Cultures A83543.1, A83543.3, A83543.4 and A83543.5 have been deposited and made part of the stock culture collection of the Midwest Area Northern Regional Research Center, Agricultural Research Service, United States Department of Agriculture, 1815 North University Street, Peoria, Ill., 61604, from which they are available to the public under the following accession numbers:

| NRRL No. | Strain No. |
|---|---|
| 18395 | A83543.1 |
| 18537 | A83543.3 |
| 18538 | A83543.4 |
| 18539 | A83543.5 |

Taxonomic studies of culture A83543.1 were carried out by Frederick P. Mertz of the Lilly Research Laboratories. Based on these studies, the microorganisms A83543.1, A83543.3, A83543.4 and A83543.5 are classified as members of a new species of the genus *Saccharopolyspora*, which is called *Saccharopolyspora spinosa* sp. nov. This classification is based on direct laboratory comparisons and examination of published descriptions of similar species.

METHODS USED

The methods followed were those recommended by the International *Streptomyces* Project (ISP) for the characterization of *Streptomyces* species [E. B. Shirling and D. Gottlieb, "Methods for Characterization of *Streptomyces* Species," *Int. J. Syst. Bacteriol.* 16:313–340 (1966)] and those recommended for the characterization of *Nocardia* species by R. E. Gordon, D. A. Barnett, J. E. Handerhan and C. H. Pang, "*Nocardia coeliaca, Nocardia autotrophica,* and the *Nocardin* Strain", *Int. J. Syst. Bacteriol.* 24(1), 54–63 (1974).

ISCC-NBS Centroid Color Charts, standard sample No. 2106 (National Bureau of Standards, 1958, U.S. Department of Commerce, Washington, D.C.) were used to assign color names to the reverse side and to aerial hyphae.

Morphology was studied using an optical light microscope and a scanning electron microscope (SEM).

The isomer of diaminopimelic acid (DAP) and the carbohydrates in hydrolysates of whole cells were established by the chromatographic methods of Becker et al. [B. Becker, M. P. Lechevalier, R. E. Gordon and H. E. Lechevalier, "Rapid Differentiation between *Nocardia* and *Streptomyces* by Paper Chromatography of Whole-cell Hydrolysates," *Appl. Microbiol.* 12, 421–423 (1964)] and of Lechevalier and Lechevalier [M. P. Lechevalier and H. Lechevalier, "Chemical Composition as a Criterion in the Classification of Aerobic Actinomycetes," *Int. J. Syst. Bacteriol.* 20, 435–443 (1970)].

Phospholipids were determined by the procedure of M. P. Lechevalier and H. Lechevalier [in *A University Laboratory Approach,* Dietz and Thayer (eds.), Society for Industrial Microbiology Special Publication No. 6, Arlington, Va., pp. 227–233 (1980)].

Menaquinone composition was determined by following the procedures of R. M. Kroppenstedt [in *Chemical Methods in Bacterial Systematics,* M. Goodfellow and D. E. Minnikin (eds.), 1985, pp. 173–196] and M. D. Collins (ibid., pp. 267–285).

Resistance to antibiotics was measured by padding antibiotic sensitivity discs onto the surface of seeded ISP No. 2 agar plates.

Starch hydrolysis was determined by testing for the presence of starch with iodine on ISP No. 4 (inorganic salts-starch) agar plates.

Fatty acid analysis was done using the HP 5898A Microbial Identification System [see L. Miller and T. Berger, "Bacterial Identification by Gas Chromatography of Whole Cell Fatty Acids," Hewlett-Packard Application Note 228-41, 8pp. (1985)].

Fatty acid methyl esters were made from lyophilized whole cells grown under identical conditions.

Principal component analysis was two dimensional and computer generated. Units of measurement in the principal component pilot (shown in FIG. 12) are standard deviations.

Mycolic acids were determined by the methods proposed by Minnikin [D. E. Minnikin, I. G. Hutchinson and A. B.

Caldicott, "Thin-Layer Chromatography of Methanolysates of Mycolic Acid-Containing Bacteria," *J. Chromatography* 188, 221–233 (1980)].

CULTURAL CHARACTERISTICS

Culture A83543.1 grew well on both complex and defined media. The culture produced aerial mycelia on all the media used. The aerial spore-mass color was predominantly light yellowish-pink, but was white on a number of the media.

The reverse side was yellow to yellow-brown. No distinctive pigmentation was present. A soluble brown pigment was released into the medium in some media.

The cultural characteristics are summarized in Table VI.

TABLE VI

Cultural Characteristics of A83543.1[a]

| Medium | Growth | Reverse Color | Aerial Mycelium Growth | Color | Soluble Pigment |
|---|---|---|---|---|---|
| ISP medium 2 | Abundant | 76. l. yBr. | Abundant | 92. yWhite | None |
| ISP medium 3 | Good | 264. l. Gray | Good | 263. White | None |
| ISP medium 4 | Good | 92. yWhite | Good | 263. White | None |
| ISP medium 5 | Abundant | 73. p. OY | Abundant | 31. p. yPink | l. Brown |
| ISP medium 7 | Abundant | 77. m. yBr | Abundant | 31. p. yPink | l. Brown |
| AIA Agar[b] | Abundant | 89. p. Y | Abundant | 31. p. yPink | Brown |
| ATCC No. 172 | Abundant | 92. yWhite | Abundant | 31. p. yPink | None |
| Bennetts | Abundant | 92. yWhite | Abundant | 31. p. yPink | l. Brown |
| Calcium-malate | Good | 73. p. OY | Fair | 9. pk. White | Brown |
| Chitin | Fair | 92. yWhite | Fair | 263. White | None |
| Czapek | Good | 92. yWhite | Good | 263. White | None |
| Emerson | Abundant | 76. l. yBr | Abundant | 31. p. yPink | Brown |
| Glucose-Asparagine | Good | 90. gy. Y | Fair | 31. p. yPink | l. Brown |
| Glycerol-Glycine | Abundant | 78. d. yBr | Abundant | 80. gy. yBr | d. Brown |
| Nutrient | Abundant | 90. gy. Y | Abundant | 31. p. yPink | l. Brown |
| TPO[c] | Abundant | 90. gy. Y | Abundant | 31. p. yPink | None |
| TWA[d] | Fair | 93. y Gray | Poor | 263. White | None |
| YDA[e] | Abundant | 77. m. yBr | Fair | 9. pk. White | d. Brown |

[a]Incubated at 30° C. for 21 days.
[b]Actinomycete Isolation Agar, Difco.
[c]Tomato paste oatmeal agar. In The Actinomycetes, vol. 2, S. A. Waksman, The Williams and Wilkins Co., Baltimore, 1961).
[d]Tap water agar (Gordon, Barnett, Handerhan and Pang, supra).
[e]Yeast dextrose agar (Gordon, Barnett, Handerhan and Pang, supra).

MORPHOLOGICAL CHARACTERISTICS

Culture A83543.1 produced an extensive substrate mycelium that fragmented in liquid fermentation. No fragmentation was observed when the culture was grown on agar media.

White circular colonies, 8–10 mm in diameter with raised center and yellow-brown reverse color, were observed when the culture was plated on ISP medium 1.

Well-formed aerial hyphae were present on most of the media. The aerial hyphae were segmented into long chains of spores arranged as hooks and open loops. Spirals were also observed, but they were short and incomplete.

The general morphology was Rectus-flexibilis (RA).

Aerial hyphae had a distinctive bead-like appearance, with many empty spaces in the spore chain. This feature demonstrated that a spore sheath encased the spore chain. This spore sheath was covered with very distinctive spines. The spines were approximately 1 µm long and were rounded on the end.

The spore shape was oblong and averaged approximately 1.1×1.5 µm in size. The spore-chain length was well over 50 spores. No zig-zag characteristics, sclerotia, sporangia or motile cells were observed.

PHYSIOLOGICAL CHARACTERISTICS

Culture A83543.1 produced acid from the following carbohydrates: adonitol, D-arabinose, erythritol, fructose, glucose, glycerol, mannitol, mannose, ribose and trehalose.

The culture did not produce acid from: L-arabinose, cellobiose, cellulose, dextrin, dulcitol, ethanol, galactose, glycogen, inositol, inulin, lactose, maltose, melizitose, melebiose, α-methyl-D-glucoside, raffinose, L-rhamnose, salicin, sorbitol, L-sorbose, sucrose, xylitol or xylose.

Growth was observed with galactose, maltose and melizitose, but no acid was produced from these carbohydrates.

Culture A83543.1 used the following organic acids as sodium salts: acetate, butyrate, citrate, formate, lactate, malate, propionate, pyruvate and succinate. The culture did not use benzoate, mucate, oxalate or tartrate.

A83543.1 decomposed allantoin, calcium malate, casein, elastin, hippurate, hypoxanthine, testosterone, L-tyrosine and urea. It was unable to decompose adenine, esculin, guanine, starch or xanthine.

A83543.1 produced catalase, phosphatase, urease and $H_2S$. It liquefied gelatin and reduced nitrate. It was not resistant to lysozyme and did not produce melanoid pigments. It neither peptonized nor hydrolyzed skim milk. A83543.1 tolerated levels of NaCl up to and including 11%. It was unable to survive 50° C. for 8 hours, but grew at temperatures between 15° and 37° C.

A83543.1 was resistant to cephalothin (30 µg), penicillin G (10 units) and rifampin (5 µg). It was sensitive to bacitracin (10 units), gentamicin (10 µg), lincomycin (2 µg), neomycin (30 µg), oleandomycin (15 µg), streptomycin (10

μg), tetracycline (30 μg), tobramycin (10 μg) and vancomycin (30 μg).

CELL-WALL ANALYSIS

Hydrolyzed whole cells of A83543.1 contained meso-diaminopimelic acid. Diagnostic sugars in the whole-cell extracts were galactose and arabinose. Thus, A83543.1 has a Type IV cell-wall pattern and a Type A sugar pattern (Lechevalier and Lechevalier, supra). The cells do not contain mycolic acids.

Phospholipid determinations on the whole cells indicated the presence of phosphatidyl choline and cardiolipin. No phosphatidyl ethanolamine was detected. Thus, A83543.1 has a Type PIII phospholipid pattern [M. P. Lechevalier, A. E. Stern and H. A. Lechevalier, "Phospholipids in the Taxonomy of *Actinomycetes,*" in *Actinomycetes, Zbl. Bakt. Suppl.* 11, K. P. Schaal and G. Pulverer (eds), Gustav Fischer Verlag, New York, 1981].

The major menaquinone detected was MK-9($H_4$). A minor amount of MK-9($H_6$) was observed.

PHAGE PLATING

A number of *Streptomyycete*, *Saccharopolyspora* and *Amycolatopsis* phages were plated on A83543.1. No plaques were observed.

IDENTITY OF A83543.1

As discussed, supra, culture A83543.1 has a type IV cell-wall pattern and a type A whole-cell sugar pattern. The following thirteen genera have this pattern of cell chemistry: *Nocardia, Rhodococcus, Corynebacterium, Caseobacter, Mycobacterium, Faenia (Micropolyspora), Pseudonocardia, Saccharomonospora, Saccharopolyspora, Actinopolyspora, Amycolata, Amycolatopsis* and *Kibdelosporangium*. These genera are distinguished by the presence or absence of mycolic acids, by fatty acid composition, and by phospholipid and menaquinone types. *Faenia, Pseudonocardia* and *Saccharopolyspora* have chemotaxonomic characteristics identical to those of A83543.1, but these genera differ from A83543.1 in morphological and cultural properties.

The genus *Faenia (Micropolyspora)* has smooth spores and short spore chains which are borne on both aerial and substrate hyphae. Its aerial hyphae are sparse and white in color. It is a thermophile which grows at 60° C. A83543.1 has none of these properties and thus differs from *Faenia*.

The genus *Pseudonocardia* has spores on both aerial and substrate hyphae. It is distinguished by acropetal budding and blastospores. It has a characteristic zig-zag morphology of the hyphae. The hyphae have been described as articulated but non-septate [see A. Henssen and D. Schafer, "Amended Description of the Genus *Pseudonocardia* Henssen and Description of a New Species *Pseudonocardia spinosa* Schafer," *Int. J. Syst. Bacteriol.* 21:29–34 (1971)]. It grows very slowly. Fragmentation is absent or rarely observed. A83543.1 has none of these properties.

The genus *Saccharopolyspora* is characterized by a spore sheath and a distinctive bead-like appearance of the spore chain. This feature is very prominent in A83543.1. Fragmentation has also been observed with the genus *Saccharopolyspora*. The type species, *S. hirsuta*, was isolated from sugar-cane bagasse. The parent culture from which A83543.1 was obtained was isolated from a sugar mill. Since A83543.1 has many properties of this genus, it is, therefore, considered to be a strain of *Saccharopolyspora*.

The only validly published species in the genus *Saccharopolyspora* are *S. erythraea* and *S. hirsuta*. Known subspecies are *S. hirsuta* subsp. *taberi* and *S. hirsuta* supra. *kobensis*. A83543.1 differs from these strains in either aerial and reverse color or in production of soluble pigments.

Biochemical similarity was measured by constructing a table of similarity coefficients based on as many biochemical measurements as possible. The coefficient of Jaccard Sj and the simple matching coefficient $S_{sm}$ were used [see W. Kurylowicz, A. Paszkiewicz, W. Woznicka, W. Kurzatkowski and T. Szulga, "Numerical Taxonomy of *Streptomycetes,*" Polish Medical Publishers, Warsaw, 1975, p. 37].

Table VIII summarizes these similarity coefficients.

TABLE VII

Similarity Coefficients For A83543.1 and Saccharopolyspora species

| Culture | $S_{sm}$ | Sj |
| --- | --- | --- |
| A83543.1 | 100 | 100 |
| S. hirsuta subsp. taberi | 68 | 57 |
| S. hirsuta subsp. kobensis | 67 | 60 |
| S. erythraea | 63 | 54 |
| S. hirsuta | 55 | 50 |

Fatty acid analysis of A83543.1 and the known *Saccharopolyspora* species showed that each has both saturated and branched-chain fatty acids. The fatty acid composition of A83543.1 is similar, but not identical, to that of the other species. Table VIII compares the fatty acid compositions of A83543.1 and the known *Saccharopolyspora* species.

TABLE VIII

Percentage Fatty Acid Composition of A83543.1 and Saccharopolyspora Strains

| Fatty Acid | A83543.1 | S. erythraea | S. hirsuta | S. hirsuta subsp. kobensis |
| --- | --- | --- | --- | --- |
| 15:0 Iso | 11.80 | 17.86 | 15.44 | 17.94 |
| 15:0 Anteiso | 0.64 | 1.33 | 1.38 | 1.25 |
| 16:0 Iso | 22.47 | 25.70 | 15.61 | 19.05 |
| 16:1 Trans 9 | 1.15 | — | 4.14 | 2.63 |
| 17:1 Iso F | 7.22 | 7.97 | — | — |
| 17:1 Iso G | — | — | 3.75 | 6.82 |
| 17:0 Iso | 17.59 | 13.37 | 26.26 | 19.41 |
| 17:0 Anteiso | 15.30 | 12.46 | 14.19 | 12.72 |
| 17:1 B | 4.77 | 1.90 | — | 0.67 |
| 17:1 C | 1.65 | — | 2.70 | 1.81 |
| 17:0 | 2.74 | 1.01 | 1.43 | 0.94 |
| 16:1 2OH | 1.27 | 2.07 | 4.74 | 4.85 |
| 18:1 Iso F | 7.57 | 11.31 | 6.83 | 7.47 |
| TBSA 10Me 18:0[a] | 1.15 | 1.34 | 1.77 | 1.00 |

[a]TBSA = tuberculostearic acid

Principal component analysis of the fatty acid compositions shown in Table VIII show sufficient scattering to suggest the cultures are all distinct species within the same genus. The principal component plot is presented in FIG. 12.

Table IX compares the physiological characteristics of A83543.1 to those of the existing *Saccharopolyspora* species and subspecies.

TABLE IX

Differential Physiological Characteristics of A83543.1 and Saccharopolyspora Species

| Characteristic | A83543.1 | S. erythraea | S. hirsuta | S. hirsuta subsp. taberi | S. hirsuta subsp. kobensis |
|---|---|---|---|---|---|
| Decomposition of: | | | | | |
| adenine | − | + | + | + | + |
| esculin | − | + | + | + | + |
| starch | − | + | + | + | + |
| xanthine | − | + | + | + | + |
| allantoin | + | − | − | − | ND |
| Nitrate reduction | + | + | − | + | + |
| Phosphatase | + | − | + | − | ND |
| Utilization of: | | | | | |
| benzoate | − | − | + | − | ND |
| mucate | − | − | + | − | ND |
| oxalate | − | − | + | − | ND |
| Temperature range (°C.) | 15–37 | 20–42 | 25–50 | 20–42 | 20–42 |
| NaCl tolerance (%) | 11 | ND* | 15 | ND | 12 |
| Acid produced from: | | | | | |
| arabinose | + | + | − | + | − |
| cellobiose | − | + | + | + | + |
| dextrin | − | + | + | + | ND |
| galactose | − | + | + | + | + |
| inositol | − | + | + | + | − |
| maltose | − | + | + | + | + |
| melezitose | − | + | − | + | ND |
| Acid produced from: | | | | | |
| melibiose | − | + | ND | − | ND |
| raffinose | − | + | + | + | + |
| rhamnose | − | + | + | + | − |
| salicin | − | + | − | − | ND |
| sucrose | − | + | + | + | + |
| xylose | − | + | + | − | − |
| lactose | − | − | + | − | ND |
| α-Me-D-glucoside | − | − | + | + | ND |
| sorbitol | − | − | + | − | − |
| inulin | − | ND | + | ND | + |

*ND = not done

The comparisons made indicate that A83543.1 differs sufficiently from the previously described species of Saccharopolyspora, to be a new species of Saccharopolyspora for which the name Saccharopolyspora spinosa has been selected. The name spinosa reflects the spiny spore ornamentation of this species.

The A83543.3, A83543.4 and A83543.5 strains are sufficiently similar macroscopically to the A83543.1 strain to be classified as strains of Saccharopolyspora spinosa. The four strains differ in the amount of A83543 they produce. The A83543.3 strain produces approximately four-fold more A83543 than the A83543.1 strain; and the A83543.4 and A83543.5 strains produce approximately eight to nine-fold more than the A83543.1 strain produces.

As is the case with other organisms, the characteristics of the A83543-producing cultures of this invention, Saccharopolyspora spinosa NRRL 18395, NRRL 18537, NRRL 18538 and NRRL 18539, continue to be subject to variation. Thus, mutants of these strains may be obtained by physical and chemical methods known in the art. For example, other strains can be obtained by treatment with chemicals such as N-methyl-N'-nitro-N-nitrosoguanidine. Natural and induced mutants of the Saccharopolyspora spinosa NRRL 18395, NRRL 18537, NRRL 18538 and NRRL 18539 strains which retain the characteristic of producing a recoverable amount of A83543 are part of this invention.

The culture medium used to grow the Saccharopolyspora spinosa culture can be any one of a number of media. For economy in production, optimal yield, and ease of product isolation, however, certain culture media are preferred. Thus, for example, preferred carbon sources in large-scale fermentation are glucose and maltose, although ribose, xylose, fructose, galactose, mannose, mannitol, soluble starch, potato dextrin, methyl oleate, oils such as soybean oil and the like can also be used.

Preferred nitrogen sources are cottonseed flour, peptionized milk and digested soybean meal, although fish meal, corn steep liquor, yeast extract, enzyme-hydrolyzed casein, beef extract, and the like can also be used.

Among the nutrient inorganic salts which can be incorporated in the culture media are the customary soluble salts capable of yielding zinc, sodium, magnesium, calcium, ammonium, chloride, carbonate, sulfate, nitrate and like ions.

Essential trace elements necessary for the growth the development of the organism should also be included in the culture medium. Such trace elements commonly occur as impurities in other substituents of the medium in amounts sufficient to meet the growth requirements of the organism.

Usually, if foaming is a problem, small amounts (i.e., 0.2 ml/L) of an antifoam agent such as polypropylene glycol) may be added to large-scale fermentation media. In the case of the A83543-producing cultures, however, conventional defoamers inhibit A83543 production. Foaming can be controlled by including soybean oil or pluronic L-101 (BASF) in the medium (1–3%). Additional oil may be added if foaming develops.

The percentage of a particular A83543 component may be varied by media changes. For example, adding valine or isobutyric or propionic acids increases the percentage of A83543D produced.

For production of substantial quantities of A83543, submerged aerobic fermentation in stirred bioreactors is preferred. Small quantities of A83543 may be obtained by shake-flask culture. Because of the time lag in production commonly associated with inoculation of large bioreactors with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger bioreactor. The vegetative inoculum medium can be the same as that used for larger fermentations, but other media are also suitable.

A83543 is produced by the A83543-producing organisms when grown at temperatures between about 24° and about 33° C. Optimum temperatures for A83543 production appear to be about 28°–30° C.

As is customary in submerged aerobic culture processes, sterile air is blown into the vessel from the bottom while the medium is stirred with conventional turbine impellors. In general, the aeration rate and agitation rate should be sufficient to maintain the level of dissolved oxygen at or above 35%, and preferably at or above 50%, of air saturation with an internal vessel pressure of 0.34 atmospheres.

Production of the A83543 components can be followed during the fermentation by testing extracts of the broth. HPLC, using a system as described in Example 1, is a useful assay for this purpose.

Following their production under submerged aerobic fermentation conditions, the A83543 components can be recovered from the fermentation medium by methods used in the art. The A83543 produced during fermentation of the A83543-producing organism occurs in both the mycelia and the broth. A83543 appears to be lipophilic. Thus, if a substantial amount of oil is used in the fermentation, whole broth extraction is more efficient. If only small amounts of oil are used, the major portion of the A83543 is in the mycelia. In that case, more efficient recovery of A83543 is accomplished by initially filtering the medium to separate the broth from the mycelia mass (the biomass).

A83543 can be recovered from the biomass by a variety of techniques. A preferred technique involves washing the separated biomass with water to remove remaining broth, mixing the biomass with a polar solvent in which A83543 is soluble, e.g. methanol or acetone, separating and concentrating the solvent, extracting the concentrate with a nonpolar solvent and/or adsorbing it onto a reverse-phase silica gel adsorbent such as RP-C8 or RP-C18 or a high porous polymer like HP-20 and the like.

The active material is eluted from the adsorbent with a suitable solvent such as, for example, acetonitrile:methanol mixtures containing small amounts of THF.

A83543 can be separated into individual components A83543A, A83543B, A83543C, A83543D, A83543E, A83543F, A83543G, A83543H, and A83543J by similar procedures. A preferred separation procedure involves reverse-phase silica-gel ($C_{18}$ or $C_8$) chromatography.

Alternatively, the culture solids, including medium constituents and mycelium, can be used without extraction or separation, but preferably after removal of water, as a source of A83543. For example, after production of A83543, the whole fermentation broth can be dried by lyophilization, by drum-drying, or by azeotropic distillation and drying. The dried broth can then be used directly, e.g. by mixing it directly into feed premix.

INSECTICIDE AND MITICIDE ACTIVITY

The compounds of this invention are useful for the control of insects and mites. The present invention is also directed, therefore, to a method for inhibiting an insect or mite which comprises applying to a locus of the insect or mite an insect- or mite-inhibiting amount of an A83543 compound.

The A83543 compounds show activity against a number of insects and mites. More specifically, the compounds show activity against Southern armyworm, which is a member of the insect order Lepidoptera. Other typical members of this order are codling moth, cutworms, clothes moths, Indianmeal moth, leaf rollers, corn earworm, cotton bollworm, European corn borer, imported cabbageworm, cabbage looper, pink bollworm, bagworms, Eastern tent caterpillar, sod webworm and fall armyworm.

The compounds also show activity against cotton aphid, which is a member of the insect order Homoptera. Other members of the Homoptera include leafhoppers, planthoppers, pear psylla, apple sucker, scale insects, whiteflies and spittle bugs, as well as a number of other host-specific aphid species.

In addition, the A83543 compounds show activity against stable flies, blow flies and mosquitoes, which are members of the insect order Diptera. Another typical member of this order is the common house fly.

The A83543 compounds are useful for reducing populations of insects and mites, and are used in a method of inhibiting an insect or mite population which comprises applying to a locus of the insect or mite an effective insect- or mite-inactivating amount of an A83543 compound.

The "locus" of insects or mites refers to the environment in which the insects or mites live or where their eggs are present, including the air surrounding them, the food they eat, or objects which they contact. For example, plant-ingesting insects or mites can be controlled by applying the active compound to plant parts which the insects or mites eat or inhabit, particularly the foliage.

It is contemplated that the compounds might also be useful to protect textiles, paper, stored grain, or seeds by applying an active compound to such substances.

The term "inhibiting an insect or mite" refers to a decrease in the number of living insects or mites or to a decrease in the number of viable insect or mite eggs. The extent of reduction accomplished by a compound depends, of course, upon the application rate of the compound, the particular compound used, and the target insect or mite species. At least an insect-inactivating or mite-inactivating amount should be used.

The terms "insect-inactivating amount" and "mite-inactivating amount" are used to describe the amount which is sufficient to cause a measurable reduction in the treated insect or mite population. Generally an amount in the range from about 1 to about 1000 ppm (or 0.01 to 1 kg/ha) of active compound is used.

In one preferred embodiment, the present invention is directed to a method for inhibiting a susceptible insect of the order Lepidoptera which comprises applying to a plant an effective insect-inactivating amount of an A83543 compound in accordance with the present invention.

Another preferred embodiment of the invention is directed toward a method for inhibiting biting flies of the order Diptera in animals which comprises administering an effective pest-inhibiting amount of an A83543 compound orally or parenterally to the animal.

MITE/INSECT SCREEN

The A83543 compounds were tested for miticidal and insecticidal activity in the following mite/insect screen.

Each test compound was formulated by dissolving the compound in an acetone/alcohol (1:1) mixture containing 23 g of "Toximul R" (sulfonate/nonionic emulsifier blend) and 13 g of "Toximul S" (sulfonate/nonionic emulsifier blend) per liter. These mixtures were then diluted with water to give the indicated concentrations.

Two-spotted spider mites (*Tetranychus urticae* Koch) and cotton or melon aphids (*Aphis gossypii* Glover) were introduced on squash cotyledons and allowed to establish on both leaf surfaces. Other plants in the same treatment pot were left uninfested. The leaves were then sprayed with 5 mL of test solution using a DeVilbiss atomizing sprayer at 10 psi. Both surfaces of the leaves were covered until runoff and then allowed to dry for one hour. Two uninfested leaves were then excised and placed into a Petri dish containing Southern armyworm (*Spodoptera eridania* Cramer).

Additional insects were evaluated using similar formulations and evaluation procedures, with the exceptions noted.

After standard exposure periods, percent mortality was evaluated. Results are reported in the tables infra. The following abbreviations are used:

| Term | Insect/Mite | Scientific Name |
|---|---|---|
| BW | boll weevil | *Anthonomus grandis* |
| CA | cotton aphid | *Aphis gossypii* |
| CBW | cotton bollworm | *Heliothis zea* |
| CLH | corn leafhopper | *Dalbulus maidis* |
| CRW | Southern corn rootworm | *Diabrotica undecimpunctata howardi* |
| SAW | Southern armyworm | *Spodoptera eridania* |
| SM | twospotted spider mite | *Tetranychus urticae* |

TABLE X

Activity of A83543A Against Neonate CBW Larvae

| Treatment | Days[a] | Rate (ppm) | % Inhibition[b] |
|---|---|---|---|
| Topical[c] | 1 | 1.00 | 20.00 |
|  |  | 5.00 | 100.00 |
|  |  | 10.00 | 100.00 |
|  |  | 50.00 | 100.00 |
|  |  | 100.00 | 100.00 |
| Diet[d] | 4 | 1.00 | 30.00 |
|  |  | 5.00 | 100.00 |
|  |  | 10.00 | 100.00 |
|  |  | 50.00 | 100.00 |
|  |  | 100.00 | 100.00 |
| Ova[e] | 6 | 10.00 | 0.00 |
|  |  | 50.00 | 0.00 |
|  |  | 100.00 | 30.00 |
| Topical[c] | 1 | 0.50 | 10.00 |
|  |  | 1.00 | 40.00 |
|  |  | 5.00 | 80.00 |
|  |  | 10.00 | 100.00 |
|  |  | 50.00 | 100.00 |
|  |  | 100.00 | 70.00 |
| Diet | 3 | 0.50 | 15.00 |
|  |  | 1.00 | 45.00 |
|  |  | 5.00 | 100.00 |
|  |  | 10.00 | 100.00 |
|  |  | 50.00 | 100.00 |

[a]Number of days between treatment and observation
[b]Mean of two replicates tested
[c]Treated with 1 mL of formulated A83543A
[d]Diet is surface treated with A83543A, allowed to dry and infested
[e]Eggs topically treated with A83543A and held until control eggs completely hatch

TABLE XI

Percent Control of Neonate CBW Larvae by A83543 Components[1]

| Component[2] | PPM | | | |
|---|---|---|---|---|
|  | 0.5 | 1 | 5 | 10 |
| A | 55 (d) | 100 (a) | 100 (a) | 100 (a) |
| B | 35 (e) | 80 (c) | 100 (a) | 100 (a) |
| C | 5 (g) | 85 (bc) | 93 (bc) | 100 (a) |
| D | 58 (d) | 90 (ac) | 100 (a) | 100 (a) |
| E | 28 (ef) | 58 (d) | 100 (a) | 100 (a) |
| F | 0 (g) | 0 (g) | 0 (g) | 95 (ab) |
| G | 0 (g) | 0 (g) | 20 (f) | 80 (c) |

[1]Treatments with the same letter in parentheses are similar at the 0.05 level.
[2]Topical pipet method with 20 larve/replicate and 4 replicates; one day between treatment and observation.

TABLE XII

Activity of A83543A Against SAW Larvae

| Stage | Treatment | Days[a] | Rate (ppm) | % Inhibition[b] |
|---|---|---|---|---|
| Neonate | Foliar/Bushbean[c] | 3 | 1.00 | 10.00 |
|  |  |  | 5.00 | 40.00 |
|  |  |  | 10.00 | 100.00 |
|  |  |  | 50.00 | 100.00 |
|  |  |  | 100.00 | 100.00 |
| Neonate | Topical[d] | 3 | 1.00 | 0.00 |
|  |  |  | 5.00 | 60.00 |
|  |  |  | 10.00 | 100.00 |
|  |  |  | 50.00 | 100.00 |
|  |  |  | 100.00 | 100.00 |
| Neonate | Foliar/Bushbean[e] | 4 | 0.50 | 0.00 |
|  |  |  | 1.00 | 66.67 |
|  |  |  | 5.00 | 100.00 |
|  |  |  | 10.00 | 100.00 |
|  |  |  | 50.00 | 100.00 |
| Second Instar | Topical[d] | 1 | 1.00 | 0.00 |
|  |  |  | 5.00 | 0.00 |
|  |  |  | 10.00 | 0.00 |
|  |  |  | 50.00 | 80.00 |
|  |  |  | 100.00 | 100.00 |
| Second Instar | Foliar/Bushbean[d] | 4 | 1.00 | 0.00 |
|  |  |  | 5.00 | 0.00 |
|  |  |  | 10.00 | 80.00 |
|  |  |  | 50.00 | 80.00 |
|  |  |  | 100.00 | 100.00 |
| Third Instar | Topical[e] | 2 | 1.00 | 0.00 |
|  |  |  | 5.00 | 0.00 |
|  |  |  | 10.00 | 13.33 |
|  |  |  | 50.00 | 73.33 |
| Third Instar | Foliar/Bushbean[e] | 4 | 0.50 | 0.00 |
|  |  |  | 1.00 | 0.00 |
|  |  |  | 5.00 | 40.00 |
|  |  |  | 10.00 | 100.00 |
|  |  |  | 50.00 | 100.00 |
| Fifth Instar | Topical[e] | 2 | 10.00 | 0.00 |
|  |  |  | 50.00 | 0.00 |
| Fifth Instar | Foliar/Bushbean[e] | 4 | 10.00 | 0.00 |
|  |  |  | 50.00 | 0.00 |

[a]Days between treatment and observation
[b]Mean of replicates tested
[c]One replicate
[d]Two replicates
[e]Three replicates
[f]Treated topically with 1 mL of formulated A83543A

TABLE XIII

Activity of A83543A Against Adult BW

| Treatment | Rate (ppm) | % Inhibition[a] |
|---|---|---|
| Topical[b] | 1.00 | 0.00 |
|  | 5.00 | 20.00 |
|  | 10.00 | 20.00 |
|  | 50.00 | 100.00 |
|  | 100.0 | 100.00 |

[a]One replicate; observed 3 days after treatment
[b]Formulated A83543A (1 mL) poured over adult insects in a Petri plate

TABLE XIV

Activity of A83543A in Greenhouse Tests Against Various Crop Pests

| Crop | Pest | Rate (ppm) | Inhibiton[a] |
|---|---|---|---|
| Corn | CRW | 30 | 100 |
|  |  | 15 | 50 |
|  |  | 7.5 | 10 |
|  |  | 3.75 | 0 |
| Squash | SAW | 250 | 100 |
|  |  | 125 | 100 |
|  |  | 62.5 | 100 |
|  |  | 31.25 | 55 |
|  |  | 15.63 | 40 |
|  |  | 7.8 | 20 |
|  |  | 3.9 | 20 |
|  |  | 1.9 | 0 |
| Squash | SM | 250 | 70 |
|  |  | 125 | 40 |
|  |  | 62.5 | 20 |
|  |  | 31.25 | 0 |
| Squash | CA | 100 | 0 |
|  |  | 50 | 0 |
| Corn | CLH | 200 | 90 |
|  |  | 100 | 30 |
|  |  | 50 | 0 |
| Bushbean | SAW | 100 | 100 |
|  |  | 50 | 80 |
|  |  | 25 | 40 |
|  |  | 12.5 | 0 |
| Bushbean | SM | 100 | 100 |
|  |  | 50 | 80 |
|  |  | 25 | 30 |
|  |  | 12.5 | 10 |
|  |  | 6.25 | 0 |
| Squash | CA | 100 | 80 |
|  |  | 50 | 40 |
|  |  | 25 | 0 |
| Corn | CRW | 6 | 30 |
|  |  | 3 | 0 |

Table XV compares the effectiveness and persistence of A83543A treatment with that of methomyl in outdoor pot tests against Southern armyworm.

TABLE XV

Efficacy of A83543 Against *Spodoptera eridania* in Outdoor Pot Tests

| Treatment | Rate (ppm) | Days After Treatment[a] | | | |
|---|---|---|---|---|---|
|  |  | 1 | 5 | 7 | 14 |
| A83543A | 63 | 100 | 88 | 90 | 5 |
| A83543A | 125 | 100 | 88 | 95 | 90 |
| A83543A | 250 | 100 | 95 | 100 | 100 |
| A83543A | 500 | 100 | 100 | 100 | 100 |
| methomyl | 63 | 100 | 20 | 15 | 0 |
| methomyl | 125 | 100 | 35 | 40 | 20 |
| methomyl | 250 | 100 | 85 | 45 | 40 |
| methomyl | 500 | 100 | 90 | 85 | 60 |
| None |  | 0 | 0 | 0 | 0 |
| None |  | 0 | 0 | 0 | 0 |

[a]Results given as % mortality

Table XVI summarizes the LC 50's, the lethal concentrations at which test compound inhibits 50% of test insect or mite, exhibited by A83543A as compared with that exhibited by the known insecticide methomyl.

TABLE XVI

LC 50'S for A83543[a]

| Target | LC 50 (ppm) | |
|---|---|---|
|  | A83543 | methomyl |
| CRW | 15 | 6 |
| Grain Aphid | >250 | 5.4 |
| SM | 150 | 71.4 |
| SAW/Foliar | 1.3 | 11.4 |
| CBW/Contact | 0.6 | 14.5 |

[a]Corn rootworm rate in soil by wt.; all others as spray concentration.

The A83543 components were active against yellow fever mosquito (*Aedes aegypti*) larvae in standard in vitro mosquito larvicide tests. Tables XVII and XVIII summarize the activity of the components in these tests.

TABLE XVII

In Vitro Activity of A83543B and A83543C Against First Instar Mosquito Larvae

| A83543 Component | Minimal Inhibitory Concentration (mcg/mL)[a] |
|---|---|
| A | 0.016, 0.031[b] |
| B | 0.016 |
| C | 0.031 |

[a]Lowest concentration which showed 100% inhibition after 24 hr (on microtiter plates)
[b]Tests on two lots

TABLE XVIII

Activity of A83543 Components vs. Fourth Instar Mosquito Larvae[a]

| Component | Percent Control[a] |
|---|---|
| A | 60, 70[b] |
| B | 60 |
| C | 60 |
| D | 30 |
| E | 80 |
| F | 0 |
| G | 0 |

[a]At 24 hr when treated at 0.312 ppm
[b]Results of two tests

FIELD TRIALS

A83543A was evaluated in field trials. In these trials, A83543A showed activity against imported cabbage worm and cabbage looper on sprouting broccoli and against a mixture of soybean loopers (75%) and fall armyworm (25%) on soybean.

INSECTICIDAL COMPOSITIONS

The compounds of this invention are applied in the form of compositions, which are also part of this invention. These compositions comprise an A83543 compound and a phytologically acceptable inert carrier. The active component, i.e. the A83543 compound, may be present as 1) a single A83543 component, 2) a mixture of two or more components, 3) the separated A83543 mixture or 4) A83543 together with the dried portion of the fermentation medium in which it is produced, i.e. the as crude, dried fermentation broth.

The compositions are either concentrated formulations which are dispersed in water for application, or are dust or granular formulations which are applied without further treatment.

The compositions are prepared according to procedures and formulae which are conventional in the agricultural chemical art, but which are novel and important because of the presence of one or more of the compounds of this invention.

The dispersions in which the compounds or crude dried material are applied are most often aqueous suspensions or emulsions prepared from concentrated formulations of the compounds or crude material. Such water-soluble, water-suspendable or emulsifiable formulations are either solids (usually known as wettable powders) or liquids (usually known as emulsifiable concentrates or aqueous suspensions).

Wettable powders, which may be compacted to form water dipsersible granules, comprise an intimate mixture of the active compound, an inert carrier and surfactants. The concentration of the active compound is usually from about 10% to about 90% by weight. The inert carrier is usually chosen from among the attapulgite clays, the montmorillonite clays, the diatomaceous earths, or the purified silicates.

Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers.

Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol.

Suitable emulsifiers for emulsifiable concentrates are chosen from conventional nonionic surfactants, such as those mentioned above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added to increase the density and viscosity of the aqueous vehicle. It is often most effective to grind and mix the compound at the same time by preparing the aqueous mixture and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance.

Such compositions are usually prepared by dissolving the compound in a suitable solvent and applying it to a granular carrier which has been pre-formed to the appropriate particle size, in the range of from about 0.5 to 3 mm. Such compositions may also be formulated by making a dough or paste of the carrier and compound, and crushing and drying to obtain the desired granular particle size.

Dusts containing the compounds are prepared simply by intimately mixing the compound in powdered form with a suitable dusty agricultural carrier, such as kaolin clay, ground volcanic rock and the like. Dusts can suitably contain from about 1% to about 10% of the compound.

It is equally practical, when desirable for any reason, to apply the compound in the form of a solution in an appropriate organic solvent, usually a blend petroleum oil, such as the spray oils, which are widely used in agricultural chemistry.

Insecticides and miticides are generally applied in the form of a dispersion of the active ingredient in a liquid carrier. It is conventional to refer to application rates in terms of the concentration of active ingredients in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples provided. In general, concentrations of from 10 ppm to 5000 ppm of compound are expected to provide good control. With may of the compounds, concentrations of from 100 to 1000 ppm will suffice. For field crops, such as soybeans and cotton, a suitable application rate for the compounds is about 0.01 to 1 kg/ha, typically applied in 5–50 gal/A of spray formulation.

The locus to which a compound is applied can by any locus inhabited by an insect or mite, for example, vegetable crops, fruit and nut trees, grape vines, and ornamental plants.

Because of the unique ability of mite eggs to resist toxicant action, repeated applications may be desirable to control newly emerged larvae, as is true of other known acaricides.

ECTOPARASITICIDE ACTIVITY

The A83543 compounds are also active against members of the insect order Diptera.

Tables XIX–XXI summarizes in vitro studies with A83543A and A83543D.

TABLE XIX

In vitro Efficacy of A83543A Against Black Blow Fly Larvae

| Dose Level (ppm) | Activity[1] |
|---|---|
| 100 | 100 |
| 50 | 100 |
| 25 | 100 |
| 10 | 100 |
| 5 | 100 |
| 2 | 100 |
| 1 | 95 |
| 0.5 | 60 |
| 0.25 | 25 |

[1]Activity = % mortality

TABLE XX

In vitro Efficacy of A83543A Against Adult Stable Fly

| Dose Level (ppm) | 24 Hour Activity[1] | 48 Hour Activity[1] |
|---|---|---|
| 100 | 100 | 100 |
| 50 | 100 | 100 |
| 25 | 100 | 100 |
| 10 | 100 | 90 |
| 5 | 80 | 100 |
| 2 | 70 | 90 |
| 1 | 10 | 60 |
| 0.5 | 0 | 10 |

[1]Activity = % mortality

TABLE XXI

In vitro Efficacy of A83543A and A83543D[1,2]

| | A83543A | | | | A83543D | | | |
|---|---|---|---|---|---|---|---|---|
| | ASF | | LBF | | ASF | | LBF | |
| ppm | 24 hr | 48 hr | 24 hr | 48 hr | 24 hr | 48 hr | 24 hr | 48 hr |
| 10 | 80 | 100 | 100 | 100 | 50 | 100 | 100 | 100 |
| 5 | 50 | 100 | 100 | 100 | 20 | 90 | 90 | 100 |
| 2.5 | 30 | 100 | 100 | 100 | 20 | 100 | 90 | 100 |
| 1.25 | 20 | 100 | 100 | 100 | 10 | 90 | 80 | 90 |
| 0.625 | 0 | 70 | 60 | 90 | 0 | 60 | 50 | 75 |
| 0.312 | 0 | 50 | 25 | 50 | 0 | 0 | 25 | 25 |

[1]Percent insect mortality following 24 to 48 hrs. in vitro exposure to chemically added serum samples
[2]ASF = adult stable fly
LBF = blow fly larvae
ppm = parts per million In in vivo tests, the A83543 compounds showed systemic insecticidal activity in guinea pigs and sheep against larval blow fly and adult stable fly with no obvious signs of toxicity. Representative compounds A83543A and A83543D have been tested in laboratory and target animals to determine the scope of activity. The following tests are illustrative.

GUINEA PIG SYSTEMIC TEST

Adult guinea pigs are used in this test system. The compounds to be tested are dissolved in aqueous polyvinyl pyrrolidone or in polyethylene glycol 200, and an appropriate amount of the solution is administered either orally or by intraperitoneal injection. Various doses of the compound are used, as set forth in the tables infra.

Blood is drawn from the guinea pigs at 30 minutes except as noted, and the samples of blood are centrifuged. Dental wicks are saturated with the blood serum, and then exposed in Petri dishes to adult stable flies; blow fly larvae are exposed in test tubes. After 24 and 48 hours, the insects are examined, and the number of dead are counted. The results of the tests are recorded as the percent of the insects which are killed.

SHEEP SYSTEMIC TEST

Tests are carried out in sheep using the test method described supra in the Guinea Pig Test description. Test compound is administered by intraperitoneal or intravenous injection or intraruminally; blood samples are drawn at 24 hours in these tests.

The results of guinea pig and sheep systemic tests using A83543A and A83543D are summarized in Tables XXII-XXV.

A83543A did not show anthelmintic activity in sheep treated by a single intraperitoneal or intraruminal dose of 50 mg/kg of body weight, or in mice experimentally infected with the intestinal nematode *Nematospiroides dubius*, when administered orally by a single gavage at 500 mg/kg.

TABLE XXII

In Vivo Insecticidal Activity of A83543A[a]

| Guinea Pig Systemic | | | | Sheep Systemic | | | |
|---|---|---|---|---|---|---|---|
| mg/kg | LBF | ASF | Tox | mg/kg | LBF | ASF | Tox |
| 10 (IP) | 0 | 0 | N | 10 (IP) | 0 | 0 | N |
| 20 (IP) | 0 | 0 | N | 10 (IR) | 0 | 0 | N |
| 30 (IP) | 90 | 50 | N | 30 (IP) | 80 | 0 | N |
| 50 (IP) | 100 | 100 | N | 30 (IR) | 100 | 30 | N |
| 50 (OR) | 100 | 60* | N | 50 (IP) | 20 | 30 | N |
| | | | | 50 (IR) | 100 | 70 | N |
| | | | | 2 × 25 (IR) | 100 | 90 | N |
| | | | | 1.0 (IV) | 25 | 10 | N |

*5-hr blood sample; no 30-min sample taken
[a]Activity measured as % mortality
ASF = adult stable fly
LBF = blow fly larvae
Tox = toxicity to the host animal
(N = none)
IP = intraperitoneal
IR = intraruminal
IV = intravenous
OR = oral

TABLE XXIII

Systemic Insecticidal Activity of A83543A and A83543D in Guinea Pigs[a]

| Dose | | | A83543A % Activity | | A83543D % Activity | |
|---|---|---|---|---|---|---|
| (mg/kg) | Route | Bled | LBF | ASF | LBF | ASF |
| 10 | IP | 30 min | 0 | 0 | 0 | 0 |
| | | 5 hr | 0 | 0 | 0 | 0 |
| | | 24 hr | 0 | 0 | 0 | 10 |
| 20 | IP | 30 min | 0 | 0 | | |
| | | 5 hr | 0 | 0 | | |
| | | 24 hr | 0 | 0 | | |
| 30 | IP | 30 min | 90 | 50 | 0 | 0 |
| | | 5 hr | 50 | 0 | 0 | 0 |
| | | 24 hr | 30 | 0 | 0 | 0 |
| 50 | IP | 30 min | 100 | 100 | 75 | 0 |

TABLE XXIII-continued

Systemic Insecticidal Activity of A83543A and A83543D in Guinea Pigs[a]

| Dose (mg/kg) | Route | Time Bled | A83543A % Activity | | A83543D % Activity | |
|---|---|---|---|---|---|---|
| | | | LBF | ASF | LBF | ASF |
| | | 5 hr | 95 | 40 | 0 | 0 |
| | | 24 hr | 25 | 30 | 25 | 0 |
| 50 | Oral | 5 hr | 100 | 60 | | |
| | | 24 hr | 0 | 0 | | |

[a]LBF = blow fly larvae
ASF = adult stable fly
IP = intraperitoneal

In in vitro tests against the sheep intestinal nematode *Haemonchus contortus*, A83543A killed 30% of the worms at a concentration of 100 ppm.

ECTOPARASITICIDAL METHODS

The ectoparasiticidal method of this invention is carried out by administering an A83543 compound to host animals to control insect and acarina parasites. Administration to the animal may be by the dermal, oral or parenteral routes.

Parasitic insects and acarina include species that are bloodsucking as well as flesh eating and are parasitic during all of their life cycle or only part of their life cycle, such as only the larval or only the adult stage. Representative species include the following:

TABLE XXIV

Insecticidal Assay of A83543A in the Blood of Sheep Challenged with *Haemonchus contortus* - 24-hour in vitro Exposure of Insects to Serum Samples Collected from Sheep[a]

| Treatment[b] | Initial Weight (kg) | Day 0 | | 35 min | | 5 hr | | Day 1 | | Day 2 | | Day 3 | | Day 4 | | Day 5 | |
|---|---|---|---|---|---|---|---|---|---|---|---|---|---|---|---|---|---|
| | | L | A | L | A | L | A | L | A | L | A | L | A | L | A | L | A |
| 50 × 1 (IP) | 38.6 | 0 | 0 | 0 | 0 | 10 | 0 | 10 | 0 | 20 | 10 | 20 | 0 | 10 | 10 | 10 | 0 |
| 50 × 1 (IR) | 31.8 | 0 | 0 | 0 | 10 | 40 | 10 | 90 | 0 | 90 | 20 | 80 | 0 | 40 | 0 | 20 | 0 |
| 25 × 2 (IR) | 34.1 | 0 | 0 | 0 | 20 | 25 | 10 | 100 | 10 | 90 | 20 | 90 | 0 | 60 | 0 | 50 | 0 |
| 1 × 1 (IV) | 25.9 | 0 | 0 | 25 | 10 | 10 | 0 | 0 | 0 | 0 | 0 | 0 | 0 | 0 | 0 | 0 | 0 |
| Vehicle Control | 44.5 | 0 | 0 | 0 | 0 | 0 | 0 | 0 | 0 | 0 | 0 | 0 | 0 | 0 | 0 | 0 | 0 |
| Nontreated | 30.9 | 0 | 0 | 0 | 0 | 0 | 0 | 0 | 0 | 0 | 10 | 0 | 0 | 0 | 0 | 0 | 0 |

[a]L = larval blow fly
A = adult stable fly
IP = intraperitoneal
IR = intraruminal
IV = intravenous
[b]Amount (mg/kg) times number of doses administered
[c]Times post-administration at which blood is drawn

TABLE XXV

Insecticidal Assay of A83543A in the Blood of Sheep Challenged with *Haemonchus contortus* - 48 hour in vitro Exposure of Insects to Serum Samples Collected from Sheep[a]

| Treatment[b] | Initial Weight (kg) | Day 0 | | 35 min | | 5 hr | | Day 1 | | Day 2 | | Day 3 | | Day 4 | | Day 5 | |
|---|---|---|---|---|---|---|---|---|---|---|---|---|---|---|---|---|---|
| | | L | A | L | A | L | A | L | A | L | A | L | A | L | A | L | A |
| 50 × 1 (IP) | 38.6 | 0 | 20 | 10 | 0 | 10 | 10 | 10 | 0 | 20 | 30 | 20 | 10 | 20 | 20 | 25 | 0 |
| 50 × 1 (IR) | 31.8 | 0 | 0 | 0 | 10 | 75 | 30 | 100 | 60 | 100 | 70 | 100 | 20 | 40 | 20 | 25 | 0 |
| 25 × 2 (IR) | 34.1 | 0 | 10 | 0 | 30 | 50 | 10 | 100 | 90 | 100 | 90 | 100 | 70 | 90 | 30 | 75 | 30 |
| 1 × 1 (IV) | 25.9 | 0 | 0 | 25 | 10 | 10 | 20 | 0 | 0 | 0 | 0 | 0 | 0 | 0 | 0 | 0 | 0 |
| Vehicle Control | 44.5 | 0 | 10 | 0 | 0 | 0 | 20 | 0 | 10 | 0 | 0 | 0 | 20 | 0 | 0 | 0 | 0 |
| Nontreated | 30.9 | 0 | 40 | 0 | 0 | 0 | 0 | 0 | 0 | 0 | 10 | 0 | 0 | 0 | 0 | 0 | 0 |

[a]L = larval blow fly
A = adult stable fly
IP = intraperitoneal
IR = intraruminal
IV = intravenous
[b]Amount (mg/kg) times number of doses administered
[c]Times post-administration at which blood is drawn

| | |
|---|---|
| horse fly | Tabanus spp. |
| stable fly | Stomoxys calcitrans |
| black fly | Simulium spp. |
| horse sucking louse | Haematopinus asini |
| mange mite | Sarcoptes scabiei |
| scab mite | Psoroptes equi |
| horn fly | Haematobia irritans |
| cattle biting louse | Bovicola bovis |
| shortnosed cattle louse | Haematopinus eurysternus |
| longnosed cattle louse | Linognathus vituli |
| tsetse fly | Glossina spp. |
| cattle follicle mite | Demodex bovis |
| cattle tick | Boophilus microplus and B. decoloratus |
| Gulf Coast tick | Amblyomma maculatum |
| Lone Star tick | Amblyomma americanum |
| ear tick | Otobius megnini |
| Rocky Mountain wood tick | Dermacentor andersoni |
| screwworm fly | Cochliomyia hominivorax |
| assassin bug | Reduvius spp. |
| mosquito | Culiseta inornata |
| brown ear tick | Rhipicephalus appendiculatus |
| African red tick | Rhipicephalus evertsi |
| bont tick | Amblyomma sp. |
| bont legged tick | Hyalomma sp. |
| hog louse | Haematopinus suis |
| chigoe | Tunga penetrans |
| body louse | Haematopinus ovillus |
| foot louse | Linognathus pedalis |
| sheep ked | Melophagus ovinus |
| sheep scab mite | Psoroptes ovis |
| greenbottle fly | Phaenicia sericata |
| black blow fly | Phormia regina |
| secondary screw-worm | Cochliomyia macellaria |
| sheep blow fly | Phaenicia cuprina |
| bed bug | Cimex lectularius |
| Southern chicken flea | Echidnophaga gallinacea |
| fowl tick | Argas persicus |
| chicken mite | Dermanyssus gallinae |
| scalyleg mite | Knemidokoptes mutans |
| depluming mite | Knemidokoptes gallinae |
| dog follicle mite | Demodex canis |
| dog flea | Ctenocephalis canis |
| American dog tick | Dermacentor variabilis |
| brown dog tick | Rhipicephalus sanguineus |

The method of the invention may be used to protect economic and companion animals from ectoparasites. For example, the compounds may beneficially be administered to horses, cattle, sheep, pigs, goats, dogs, cats and the like, as well as to exotic animals such as camels, llamas, deer and other species which are commonly referred to as wild animals. The compounds may also beneficially be administered to poultry and other birds, such as turkeys, chickens, ducks and the like. Preferably, the method is applied to economic animals, and most preferably to cattle and sheep.

The rate, timing, and manner of effective application will vary widely with the identity of the parasite, the degree of parasiticidal attack, and other factors. Applications can be made periodically over the entire lifespan of the host, or for only a peak season of parasitic attack. In general, ectoparasite control is obtained with topical application of liquid formulations containing from about 0.00005 to 5.0% of compound, and preferably from about 0.00005 to about 1.0% of compound. Effective parasite control is achieved at administration rates of from about 5 to about 100 mg/kg.

The compounds are applied to host animals by conventional veterinary practices. Usually, the compounds are formulated into ectoparasiticidal compositions which comprise a compound and a physiologically-acceptable carrier. For example, liquid compositions may be simply sprayed on the animals for which ectoparasiticidal control is desired. The animals may also treat themselves by such devices as back rubbers, which may contain the toxicant compound in a cloth, for example, which the animal may walk against and contact. Dip tanks are also employed to administer the active agent to the host animal.

The present compounds display systemic ectoparasiticidal activity. The compounds have the ability to permeate the tissues of a host animal to which one of the compounds has been administered. Insect parasites which then consume blood or other living tissues of the host animal are thereby killed. The compounds are administered by dermal, oral or percutaneous routes and are preferably formulated prior to administration. Such formulations are well known to those skilled in the art, for example by dissolving the compound in one of many physiologically-acceptable adjuvants or diluents. Oral administration may be performed by mixing the compound in the animals' feed or drinking water, or by administering dosage forms such as tablets, capsules, boluses, or implants. Percutaneous administration is conveniently accomplished by subcutaneous, intraperitoneal and intravenous injection of an injectable formulation.

The compounds can be formulated for oral administration in the usual forms, such as drenches, tablets, or capsules. Such compositions, of course, require orally-acceptable inert carriers. The compounds can also be formulated as an injectable solution or suspension, for subcutaneous, dermal, intraruminal, intraperitoneal, intramuscular, or intravenous injection. In some applications, the compounds are conveniently formulated as one component of a standard animal feed. In this embodiment, it is usual to formulate the present compound first as a premix in which the compound is dispersed in a liquid or particulate solid carrier. The premix can contain from about 2 to 250 grams of compound per pound. The premix is in turn formulated into the ultimate feed by conventional mixing.

Since ectoparasitic attack generally takes place during a substantial portion of the host animal's lifespan, it is preferred to administer the compounds of the present invention in a form to provide sustained release over a period of time. Conventional procedures include the use of a matrix which physically inhibits dissolution, where the matrix is a waxy semisolid such as the vegetable waxes or a high molecular weight polyethylene glycol. A good way to administer the compounds is by means of a sustained-action bolus, such as those of Laby, U.S. Pat. No. 4,251,506, and Simpson, British Patent 2,059,767. For such a bolus, the compound would be encapsulated in a polymeric matrix such as that of Nevin, U.S. Pat. No. 4,273,920. Sustained release of the compounds of the present invention can also be achieved by the use of an implant such as from a silicone-containing rubber.

In order to illustrate more fully the operation of this invention, the following examples are provided:

EXAMPLE 1

A83543 HPLC Assay Method

The following analytical HPLC method is useful for monitoring the fermentation for production of A83543:

Centrifuge a sample of the whole broth, decant and remove the supernatant. Add enough methanol to the biomass to return the sample to the original volume, mix, and allow the mixture to stand a minimum of fifteen minutes. Centrifuge and filter the supernatant through a 0.45µ filter.

Alternatively, the whole broth can be extracted with acetonitrile (1:4 broth:solvent) or acetone.

HPLC System:

Column Support: 8-x 100-mm column, silica gel-4µ spherical $C_{18}$ (Nova C18, Waters)

Mobile Phase: $CH_3CN/MeOH/H_2O$ (45/45/10) containing 0.05% ammonium acetate

Flow Rate: 4 mL/min

Detection: UV at 250 nm

Retention Times: A83543A—3.6–3.7 min A83543D—4.4–4.5 min

EXAMPLE 2

Preparation of A83543 with Culture A83543.1

A. Shake-flask Fermentation

The culture *Saccharopolyspora spinosa* NRRL 18395, either as a lyophilized pellet or as a suspension maintained in liquid nitrogen, is used to inoculate a vegetative medium having composition A or B (medium B is preferred for large scale production):

| Ingredient | Amount (%) |
| --- | --- |
| VEGETATIVE MEDIUM A | |
| Trypticase soy broth* | 3.0 |
| Yeast extract | 0.3 |
| $MgSO_4.7H_2O$ | 0.2 |
| Glucose | 0.5 |
| Maltose | 0.4 |
| Deionized water | q.s. 1 liter |
| No pH adjustment | |
| *Baltimore Biological Laboratories | |
| VEGETATIVE MEDIUM B | |
| Enzyme-hydrolyzed casein* | 3.0 |
| Yeast extract | 0.3 |
| $MgSO_4.7H_2O$ | 0.2 |
| Glucose | 1.0 |
| Deionized water | q.s. 1 L | pH 6.2, adjust to 6.5 with NaOH
*NZ Amine A, Sheffield Products, P.O. Box 638 Norwich, NY 13815

Slants or plates can be prepared by adding 2.5% agar to vegetative seed medium A or B. The inoculated slant is incubated at 30° C. for from about 10 to 14 days. The mature slant culture is scraped with a sterile tool to loosen the spores and remove and macerate the mycelial mat. About one-fourth of the loosened spores and culture growth thus obtained is used to inoculate 50 mL of a first-stage vegetative seed medium. Alternatively, the first-stage medium may be inoculated from a liquid nitrogen ampoule.

When the culture is maintained in liquid nitrogen, ampoules are prepared using equal volumes of vegetative culture (48–72 hr incubation, 30° C.) and suspending medium. The suspending medium contains lactose (100 g), glycerol (200 mL) and deionized water (q.s. to 1 L).

A liquid nitrogen ampoule is used to inoculate 100 mL of vegetative medium in 500-mL Erlenmeyer flasks (or 50 mL medium in 250-mL flasks). The cultures are incubated at 30° C. for 48 hours on a shaker orbiting in a two-inch (5.08 cm) circle at 250 rpm.

The incubated culture (5% v/v inoculum) is used to inoculate 100 mL of a production medium having the following composition:

| PRODUCTION MEDIUM 1 | |
| --- | --- |
| Ingredient | Amount (%) |
| Glucose | 4 |
| Vegetable protein, partially hydrolyzed enzymatically* | 1.5–3 |
| Cottonseed flour** | 1.0 |
| $CaCO_3$ (reagent or technical grade) | 0.3 |
| Soybean oil | 1.0 |
| Tap water | q.s. 1 liter |

(Presterilization pH adjusted to 7.0 with NaOH)
*Sheftone H, Sheffield Products
**Proflo, Traders Protein, P.O. Box 840, Memphis, TN 38108

The inoculated production medium is incubated in 500-mL Erlenmeyer flasks at 28°–30° C. for 6 to 8 days on a shaker orbiting in a two-inch circle at 250 rpm.

B. Stirred Bioreactor Fermentation

In order to provide a larger volume of inoculum, 10 mL of incubated first-stage medium, prepared as described in Section A, is used to inoculate 400 mL of a second-stage vegetative medium having the same composition as that of the first-stage vegetative medium. This second-stage medium is incubated in a 2-L wide-mouth Erlenmeyer flask for about 48 hours at 30° C. on a shaker orbiting in a two-inch circle at 250 rpm.

Incubated second-stage vegetative medium (2 L) thus prepared is used to inoculate 80 to 115 liters of sterile production medium, prepared as described in Section A. Additional soybean oil is added to control foaming, if needed.

The inoculated production medium is allowed to ferment in a 165-L stirred bioreactor for 5 to 8 days at a temperature of 28° C. The airflow and agitator speed in the stirred vessel are computer controlled to maintain a dissolved oxygen level at or above 50% of air saturation.

EXAMPLE 3

Isolation of A83543A, B, C and D

Fermentation broth (225 liters), prepared as described in Example 2, was filtered using a filter aid (1% Hyflo), and the separated biomass was washed with water (~50 L). The biomass was then agitated with methanol (~100 L) for about one hour and filtered.

The methanol filtrate was concentrated to a volume of about 1 liter. The concentrate was extracted three times with diethyl ether (1 L each). The combined ether extracts were concentrated to a volume of about 200 mL.

A portion of the concentrate (8 mL) was chromatographed on a silica gel column (RP-8 Lobar, size B, E.M. Science, a Division of E.M. Industries, Inc.).

This procedure was repeated for a total of 12 runs (cycles). The instrumental set-up and execution procedure to perform the preparative chromatography in an "Autoprep" mode is described as follows:

A complete "Autoprep" HPLC system is comprised of three Rainin Rabbit HPX pumps, one pressure module, one Gilson Model 20 1B HPLC fraction collector, one ISCO-V[4] absorbance detector and one Apple Macintosh Plus computer. The complete system is arranged according to instructions given in the Dynamax HPLC Method Manager manual from Rainin Instrument Company, Inc. The "Autoprep" HPLC configuration takes advantage of system automation to permit preparative separations to be run repetitively under virtually identical conditions with virtually identical results. Collecting and pooling corresponding fractions from multiple runs provide chromatographic capacity without the need for a large column.

Two solvent mixtures (A) and (B) are used in the isocratic mode at a flow rate of 8.0 mL/min.

| Solvent Systems | | |
|---|---|---|
| | Amount (mL) | |
| Solvent | A | B |
| $CH_3OH$ | 95 | 100 |
| $CH_3CN$ | 95 | 100 |
| $H_2O$ | 10 | — |

The isocratic mixture used contains 60% of solvent B.

The runtime for each cycle is 28.0 minutes. The eluates from the first 16 minutes of each run are discarded. The following eluates are collected in 6 time-factions, 2 minutes (16 mL) each.

The automatically combined fractions from each of the 12 cycles resulted in 6 final fractions (chromatographic cuts).

The presence of the active A83543 compounds is determined by analyzing each final fraction for mosquito larvae activity and also by analytical HPLC.

The active fractions are then combined according to their activity and HPLC profiles and are further purified, using the same "Autoprep" HPLC and solvent system, but with a high resolution, 21.4-mm×25-cm preparative column (Rainin Dynamax), prepacked with 8μ C-18 reversed phase silica gel, to give A83543 components A, B, C and D. Factors A and D crystallize from $CH_3OH/H_2O$.

EXAMPLE 4

Purification of A83543A and D

Fermentation broth (10 L) was prepared as described in Example 2 Sect. A, except that 1) 200 mL of production medium was used in 1-L flasks; 2) soybean oil was omitted from the production medium; and 3) incubation was at 30° for 4–6 days. The broth was filtered. The filtrate, containing 4 mcg of A83543A/mL and no detectable quantities of A83543B, C, or D/mL, was discarded.

The biomass was washed with water and extracted for one hour with methanol. The extract (7 L) contained 72 mcg of A83543A/mL and 7 mcg of A83543D/mL.

The methanol extract was concentrated to a volume of 5 L, and added to HP-20 resin (150 mL, Mitsubishi Chemical Industries, Ltd., Japan) in water (2 L). This mixture was stirred for one hour.

The HP-20 resin mixture was then placed in a glass column. The initial effluent and the eluate using methanol:water (1:1, 1 L) were not active. The second eluate using methanol:water (7:3, 1 L) contained trace quantities of A83543A. The following eluate using methanol (1 L) contained the A83543A and A83543D activity.

The methanol eluate was concentrated and combined with 2 similar fractions from other work-ups and concentrated to dryness. The residue was dissolved in 75 mL of methanol:THF (4:1) and precipitated by addition into 10 volumes of acetonitrile. The mixture was filtered, and the filtrate was concentrated to dryness.

The residue was dissolved in methanol (25 mL) and applied to a 5.5-x 90-cm column of LH-20 Sephadex (Pharmacia LKB Biotechnology Inc., U.S.A.), prepared in methanol, collecting and analyzing 125 25-mL fractions, using the HPLC procedure described in Example 1.

Fractions containing the desired compounds were combined and concentrated. The residue was dissolved in methanol (10 mL) and applied to a 41.1-mm×25-cm preparative column prepacked with 8μ C-18 reversed phase silica gel (Rainin Dynamax).

The column was conditioned in methanol:acetonitrile:water (37.5:37.5:25). After sample application, the column was developed using a 180-min linear gradient of the following solvents:

| Solvent System | | |
|---|---|---|
| | Amount (mL) | |
| Solvent | A | B |
| $CH_3OH$ | 37.5 | 45 |
| $CH_3CN$ | 37.5 | 45 |
| $H_2O$ | 25 | 10 |

The gradient was run from 100% A to 100% B, collecting 25-mL fractions.

Fractions containing A83543A were pooled, concentrated to dryness, dissolved in t-BuOH (5 mL) and lyophilized to give 778 mg of pure A83543A.

Fractions containing A83543D were combined with D-containing fractions from 6 similar separations and were concentrated and chromatographed as described supra, using the same column but different solvents. The column was conditioned in methanol:acetonitrile:water(40:40:20). The solvent systems used to develop the column in a 180-min linear gradient operation were:

| Solvent Systems | | |
|---|---|---|
| | Amount (mL) | |
| Solvent | A | B |
| $CH_3OH$ | 40 | 95 |
| $CH_3CN$ | 40 | 95 |
| $H_2O$ | 20 | 10 |

Fractions containing A83543D were combined and concentrated. The residue was dissolved in t-BuOH (5 mL) and lyophilized to give 212 mg of A83543D.

EXAMPLE 5

Isolation of A83543 Components E,F,G,H and J and the Pseudoaglycone of A

Fermentation broth (8 L), prepared using procedures similar to those described in Example 2, was treated as described in Example 4. Fractions from the LH-20 Sephadex column containing the desired compounds were combined with corresponding fractions from similar fermentations. Since components E, F, G, H, J and the pseudoaglycone of A are produced in very small quantities, numerous fermentations are required to provide sufficient quantities for further purification.

A pool of minor factors, prepared in this manner and containing approximately 1.6 grams of solid material, was applied to an HPLC column (Rainin Dynamax) prepacked with 8 micron C-18 reversed phase silica gel (ODS), as described in Example 4. The column was conditioned in $CH_3OH:CH_3CN:H_2O$ (75:75:50), and the gradient was run from 100% of solvent (A) to 50% (B): with the following solvent systems:

| | Solvent Systems | |
|---|---|---|
| | Amount (%) | |
| Solvent | A | B |
| $CH_3OH$ | 75 | 95 |
| $CH_3CN$ | 75 | 95 |
| $H_2O$ | 50 | 10 | collecting 25-mL fractions. The following fractions were pooled:

| Pool | Fractions |
|---|---|
| 1 | 31–44 |
| 2 | 45–63 |
| 3 | 64–69 |
| 4 | 70–80 |
| 5 | 81–130 |
| 6 | 131–160 |

A portion of pool 5 (100 mL) was concentrated to a residue, dissolved in methanol (1 mL) and applied to a 21.4-mm× 250-mm HPLC column (Rainin Dynamax), as described in Example 3. The column was conditioned using solvent system (A) of the following solvent systems:

| | Solvent Systems | |
|---|---|---|
| | Amount (%) | |
| Solvent | A | B |
| $CH_3OH$ | 30 | 95 |
| $CH_3CN$ | 30 | 95 |
| $H_2O$(1N $NH_4OAC$, pH 5.0) | 40 | — |
| $H_2O$ | — | 10 | and developed using a 120-minute linear gradient from 100% solvent (A) to 50% of solvent (B), collecting 15-mL fractions at 7.5 mL/min. Elution was continued at 50% (B) for an additional 60 minutes. The following fractions were pooled:

| Pool | Fractions | Component |
|---|---|---|
| 1 | 37 | F |
| 2 | 38–48 | E |
| 3 | 52–63 | B, G |
| 4 | 65–70 | H, J |

These pools were combined with pools from other chromatographic runs using similar starting materials. The combined pools were further purified using column chromatography, as described supra; desalted in HP-20 resins, using standard techniques; and concentrated and lyophilized to give the following components:

| Component | Quantity (mg) | Mol. Wt* |
|---|---|---|
| E | 249 | 717 |
| F | 4 | 717 |
| G | 104 | 731 |
| H, J | 87 | 717 |
| Pseudo A | 288 | 590 |

*by mass spectrometry

EXAMPLE 6

Preparation of A83543 with Culture A83543.3

A. Shake-flask Fermentation

Using procedures like those of Example 2, Section A, the culture *Saccharopolyspora spinosa* NRRL 18537 is cultivated in shake flasks, but using vegetative medium C as follows:

| VEGETATIVE MEDIUM C | |
|---|---|
| Ingredient | Amount |
| Enzyme-hydrolyzed casein* | 30.0 g |
| Yeast extract | 3.0 g |
| $MgSO_4.7H_2O$ | 0.2 g |
| Glucose | 10.0 g |
| Glycerol | 20 mL |
| Deionized water | q.s. 1 L | pH 6.6, adjust to 7.0 with NaOH
*NZ Amine A

B. Stirred Bioreactor Fermentation

Liquid nitrogen ampoules of the culture are prepared as described in Example 2, using the general procedures of Sect. B. One ampoule is used to inoculate a first-stage vegetative culture (50 mL of medium C in 250-mL flasks), which is incubated for about 48–72 hours. Incubated first-stage culture is used to inoculate (10-mL inoculum) a second-stage culture (400 mL of medium C in 2-L flasks), which in incubated for about 48 hrs. The incubated second-stage culture (5 L) is used to inoculate a production medium (115 L) having the following composition:

| PRODUCTION MEDIUM II | |
|---|---|
| Ingredient | Amount (g/L) |
| Glucose | 80 |
| Peptonized milk* | 20 |
| Cottonseed flour** | 20 |
| $CaCO_3$ | 5 |
| Methyl oleate | 30 mL/L |
| Tap water | q.s. to 1 L |

*Peptonized Milk Nutrient, Sheffield Products; additional continuous feed, beginning the fourth day, at a rate of 5 mg/mL/day, may be used.
**Proflo
(Presterilization pH adjusted to 7.0 with NaOH)

The inoculated production medium is allowed to ferment in a 165-L stirred bioreactor for about 8 to 10 days, or longer, at a temperature of 30° C. Dissolved oxygen (DO) levels are regulated by computerized systems set to maintain the DO level above 50% of air saturation as described in Example 2, Section B.

EXAMPLE 7

Preparation of A83543 with Culture A83543.5

A. Shake-flask Fermentation

Using procedures like those of Example 2, Section A, the culture *Saccharopolyspora spinosa* NRRL 18539 is cultivated in shake flasks, using vegetative medium B.

B. Stirred Bioreactor Fermentation

Liquid nitrogen ampoules of the culture are prepared as described in Example 2, using the general procedures of Sect. B. One ampoule is used to inoculate a first-stage vegetative culture (50 mL of medium B in 250-mL flasks), which is incubated for 48 to 72 hours. Incubated first-stage culture is used to inoculate (10-mL inoculum) a second-stage culture (400 mL of medium B in 2-L flasks), which is incubated for about 48 hr. The incubated second-stage culture (2 L) is used to inoculate a production medium (115 L) having one of the following compositions:

| PRODUCTION MEDIUM III | |
|---|---|
| Ingredient | Amount (g/L) |
| Glucose | 80 |
| Vegetable protein, partially hydrolyzed enzymatically* | 20 |
| Cottonseed flour** | 10 |
| CaCO$_3$ | 5 |
| Methyl oleate | 30 mL/L |
| Tap water | q.s. to 1 L |

*Sheftone H
**Proflo
(Presterilization pH adjusted to 7.0 with NH$_4$OH)

| PRODUCTION MEDIUM IV | |
|---|---|
| Ingredient | Amount (Percent) |
| Glucose | 8 |
| Cottonseed flour* | 3 |
| Peptionized Milk** | 2 |
| Corn steep liquor | 1 |
| CaCO$_3$ (tech. grade) | 0.5 |
| Methyl oleate | 3.0 |
| Tap water | q.s. to 1 L |

*Proflo
**Peptonized Milk Nutrient
(Presterilization pH adjusted to 7.0 with NaOH)

The inoculated production medium is allowed to ferment in a 165-L stirred bioreactor for about 8 to 10 days, or longer, at a temperature of 30° C. DO levels are regulated as described in Example 6.

EXAMPLE 8

Preparation of A83543 with Culture A83543.4

Using procedures like those of Examples 2 and 7, the culture *Saccharopolyspora spinosa* NRRL 18538 is cultivated but using vegetative medium B and production medium III.

EXAMPLE 9

Fermentation broth is prepared as described in Example 8. A83543 is separated from the broth as follows:

1. Add an equal volume of acetone to the broth and filter, using a ceramic filter or filter aid with a filter press.
2. Adjust the filtrate broth to pH 10.
3. Add ethyl acetate (¼–½ the volume of the broth).
4. Recover the ethyl acetate extract by decanting off the immiscible aqueous portion; and concentrate the ethyl acetate extract to ½ volume by volume.
5. Extract the concentrated ethyl acetate solution with aqueous 0.1M tartaric acid (½ volume); and separate the phases.
6. Remove the soluble ethyl acetate from the aqueous phase by vacuum (about 5%) evaporation. Concentrate the aqueous solution, using a reverse osmosis operation.
7. Adjust the concentrated aqueous solution to pH 10–11 with sodium hydroxide.
8. Separate the precipitate by filtration; wash with water; and dry under vacuum to give A83543.

EXAMPLE 10

A83543A Pseudoaglycone

A sample of A83543 containing mostly component A (ca 100 mg) was dissolved into methanol (50 mL), water (2 mL) and concentrated HCl (3 mL). This solution was concentrated to dryness at 50° C. The residue was treated twice with diethyl ether (200 mL each), and the insoluble material was discarded. The combined ether solutions containing the crude pseudoaglycone were concentrated to dryness. The residue was dissolved in methanol (20 mL) and purified, using the AUTOPREP-HPLC system described in Example 3, to give 20 mg of pure A83543A pseudoaglycone.

EXAMPLE 11

A83543D pseudoaglycone is prepared from A83543D, using a procedure similar to that described in Example 10.

EXAMPLE 12

The following formulations are typical of the insecticidal compositions useful in this invention.

| A. Aqueous Suspension | |
|---|---|
| A-83543A | 12.5% |
| "Tergitol TMN-6" (nonionic surfactant) | 1.0% |
| "Zeosyl 200" (silica) | 1.0% |
| "AF-100" (silicon based antifoam agent) | 0.2% |
| Xanthan solution (2%) | 10.0% |
| "Makon 10" (10 moles ethyleneoxide nonylphenol surfactant) | 9.0% |
| Tap water | 66.3% |
| B. Emulsifiable Concentrate | |
| A83543D | 12.4% |
| "Exxon 200" (naphthalene solvent) | 83.6% |
| "Toximul H" (nonionic/anionic surfactant blend) | 2.0% |
| "Toximul D" (nonionic/anionic surfactant blend) | 2.0% |

EXAMPLE 13

The following exemplary compositions illustrate the sort of formulations used to practice the method of the present invention.

| A. Feed Premix | |
|---|---|
| A83543A | 10% |
| Rice hulls | 85 |
| Light mineral oil | 5 |
| B. Feed Premix | |
| A83543E | 25% |
| Alfalfa meal | 60 |
| Powdered clay | 5 |

-continued

| | | |
|---|---|---|
| Molasses | | 10 |
| C. Suspension | | |
| A83543A | | 30% |
| Naphthalenesulfonate salt | | 5 |
| Nonionic surfactant | | 5 |
| Fumed silica | | 1 |
| Water | | 59 |
| D. Drip-On Solution | | |
| A83543A | | 20% |
| Nonionic surfactant | | 0.8 |
| Propylene glycol | | 15 |
| Water | | 64.2 |
| E. Drip-On Suspension | | |
| A83543B | | 10 |
| Nonionic surfactant | | 1 |
| Light mineral oil | | 89 |
| F. Injectable Solution | | |
| A83543A | | 15% |
| Propylene glycol | | 85 |
| G. Injectable Suspension | | |
| A83543C | | 25% |
| Propylene glycol | | 15 |
| Water | | 60 |
| H. Injectable Suspension | | |
| A83543D | | 30% |
| Polyvinylpyrrolidone | | 2 |
| Water | | 68 |

We claim:

1. An ectoparasiticidal composition comprising a physiologically-acceptable inert carrier and a compound of the formula

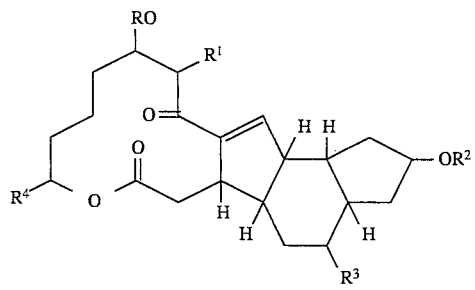

wherein
R is H or a group selected from

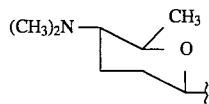 (a)

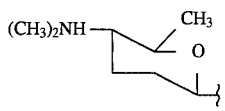 (b)

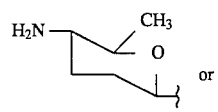 (c) or

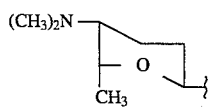 (d)

$R^2$ is

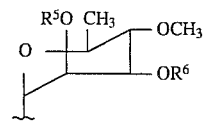

$R^1$, $R^3$, $R^5$ and $R^6$ are hydrogen or methyl;

$R^4$ is methyl or ethyl; and provided that R, $R^1$, $R^3$, $R^4$, $R^5$ and $R^6$ must be present in one of the following combinations:

| R | $R^1$ | $R^3$ | $R^4$ | $R^5$ | $R^6$ |
|---|---|---|---|---|---|
| (a) | Me | H | Et | Me | Me |
| (b) | Me | H | Et | Me | Me |
| (c) | Me | H | Et | Me | Me |
| (a) | Me | Me | Et | Me | Me |
| (a) | Me | H | Me | Me | Me |
| (a) | H | H | Et | Me | Me |
| (d) | Me | H | Et | Me | Me |
| (a) | Me | H | Et | H | Me |
| (a) | Me | H | Et | Me | H |
| H | Me | H | Et | Me | Me |
| H | Me | Me | Et | Me | Me |
| H | Me | H | Me | Me | Me |
| H | H | H | Et | Me | Me |
| H | Me | H | Et | H | Me |
| H | Me | H | Et | Me | H | or an acid addition salt of a compound wherein R is other than hydrogen.

2. An ectoparasiticidal composition of claim 1 in the form of a feed premix wherein the inert carrier is orally acceptable.

3. An ectoparasiticidal composition of claim 1 wherein the compound is selected from

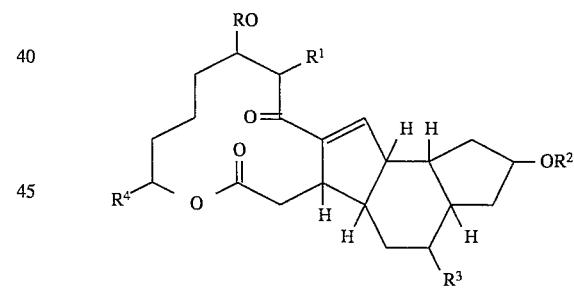

wherein
R is H or a group selected from

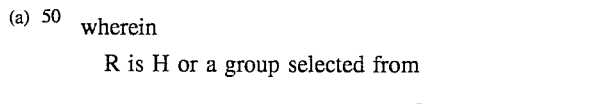 (a)

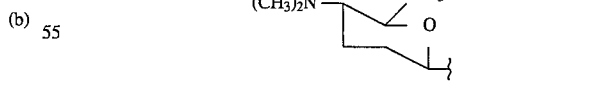 (b)

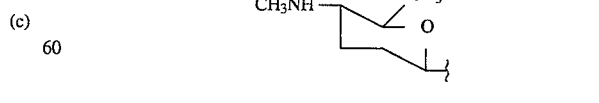 (c) or

-continued

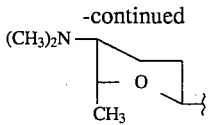

$R^2$ is

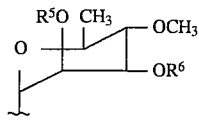

$R^1$, $R^3$, $R^5$ and $R^6$ are hydrogen or methyl;

$R^4$ is methyl or ethyl; and provided that R, $R^1$, $R^3$, $R^4$, $R^5$ and $R^6$ must be present in one of the following combinations:

| R | $R^1$ | $R^3$ | $R^4$ | $R^5$ | $R^6$ |
|---|---|---|---|---|---|
| (a) | Me | H | Et | Me | Me |
| (b) | Me | H | Et | Me | Me |
| (c) | Me | H | Et | Me | Me |
| (a) | Me | Me | Et | Me | Me |
| (a) | Me | H | Me | Me | Me |
| (a) | H | H | Et | Me | Me |
| (d) | Me | H | Et | Me | Me |
| (a) | Me | H | Et | H | Me |
| (a) | Me | H | Et | Me | H |
| H | Me | H | Et | Me | Me |
| H | Me | Me | Et | Me | Me |
| H | Me | H | Me | Me | Me |
| H | H | H | Et | Me | Me |
| H | Me | H | Et | H | Me |
| H | Me | H | Et | Me | H | or an acid addition salt of a compound wherein R is other than hydrogen
or a physiologically acceptable salt thereof.

* * * * *

UNITED STATES PATENT AND TRADEMARK OFFICE
CERTIFICATE OF CORRECTION

PATENT NO. : 5,571,901

DATED : November 5, 1996

INVENTOR(S) : LaVerne D. Boeck, Hang Chio, Tom E. Eaton, Otis W. Godfrey, Jr., Karl H. Michel, Walter M. Nakatsukasa, Raymond C. Yao It is certified that error appears in the above-identified patent and that said Letters Patent is hereby corrected as shown below:

Col. 41, line 55, " 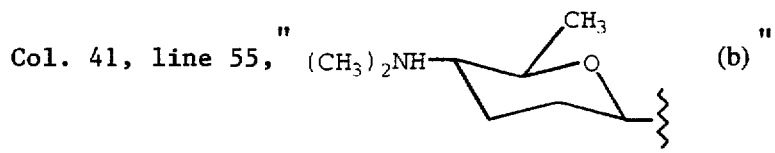 "

should read

-- 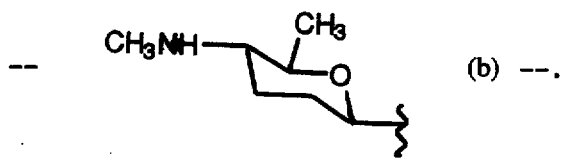 --.

Signed and Sealed this

Eighteenth Day of February, 1997

Attest:

BRUCE LEHMAN

Attesting Officer     Commissioner of Patents and Trademarks